United States Patent
Ezhov et al.

(10) Patent No.: US 11,464,467 B2
(45) Date of Patent: Oct. 11, 2022

(54) AUTOMATED TOOTH LOCALIZATION, ENUMERATION, AND DIAGNOSTIC SYSTEM AND METHOD

(71) Applicant: Diagnocat, inc., Wilmington, DE (US)

(72) Inventors: Matvey Dmitrievich Ezhov, Moscow (RU); Vladimir Leonidovich Aleksandrovskiy, Moscow (RU); Evgeny Sergeevich Shumilov, Moscow (RU); Maxim Gusarev, Tiraspol (MD); Dmitrii Morozov, Voronezh (RU); Ivan Barabanau, Mogilev (BY); Valentin Denisenkov, Saratov oblast (RU); Alexey Timonkin, Sarov (RU); Valentin Fedosov, Saint Petersburg (RU); Artem Kravtsov, Moscow (RU); Azat Akhtyamov, Moscow (RU); Vasiliy Igorevich Grachev, Moscow (RU); David Manulis, Moscow (RU); Alexandr Schadnev, Moskovskaya oblast (RU); Yan Kalika, San Francisco, CA (US)

(73) Assignee: DGNCT LLC, Miami, FL (US)

( * ) Notice: Subject to any disclaimer, the term of this patent is extended or adjusted under 35 U.S.C. 154(b) by 0 days.

(21) Appl. No.: 16/847,563

(22) Filed: Apr. 13, 2020

(65) Prior Publication Data
US 2020/0305808 A1    Oct. 1, 2020

Related U.S. Application Data

(63) Continuation-in-part of application No. 16/783,615, filed on Feb. 6, 2020, which is a continuation-in-part
(Continued)

(51) Int. Cl.
*G06K 9/00* (2022.01)
*A61B 6/14* (2006.01)
(Continued)

(52) U.S. Cl.
CPC ............ *A61B 6/145* (2013.01); *A61B 5/0022* (2013.01); *A61B 5/4842* (2013.01);
(Continued)

(58) Field of Classification Search
CPC ..... A61B 6/145; A61B 5/0022; A61B 5/4842; A61B 5/7275; A61B 5/1075;
(Continued)

(56) References Cited

U.S. PATENT DOCUMENTS

| | | | | |
|---|---|---|---|---|
| 6,102,704 A | * | 8/2000 | Eibofner | A61B 5/7475 433/29 |
| 7,596,253 B2 | * | 9/2009 | Wong | H04N 17/002 382/128 |

(Continued)

*Primary Examiner* — Van D Huynh
(74) *Attorney, Agent, or Firm* — Patent Ventures, LLC

(57) ABSTRACT

A system and method for automated localization, enumeration, and diagnoses of a tooth/condition. The system detects a condition for at least one defined localized and enumerated tooth structure within a cropped image from a full mouth series based on any one of a pixel-level prediction, wherein said condition is detected by at least one of detecting or segmenting a condition on at least one of the enumerated tooth structures within the cropped image by a 2-D R-CNN.

15 Claims, 22 Drawing Sheets

Related U.S. Application Data of application No. 16/175,067, filed on Oct. 30, 2018, now Pat. No. 10,991,091.

(51) Int. Cl.

| | | |
|---|---|---|
| *G06K 9/62* | (2022.01) | |
| *A61B 5/00* | (2006.01) | |
| *G06N 3/08* | (2006.01) | |
| *G06V 10/22* | (2022.01) | |
| *G06V 10/24* | (2022.01) | |
| *G06V 10/46* | (2022.01) | |

(52) U.S. Cl.
CPC .......... *A61B 5/7275* (2013.01); *G06K 9/6256* (2013.01); *G06N 3/08* (2013.01); *G06V 10/22* (2022.01); *G06V 10/243* (2022.01); *G06V 10/462* (2022.01); *G06V 2201/033* (2022.01)

(58) Field of Classification Search
CPC ..... A61B 5/4504; A61B 5/7267; A61B 5/743; A61B 6/501; A61B 6/14; A61B 6/4085; G06K 9/2054; G06K 9/3275; G06K 9/4671; G06K 9/6256; G06K 2209/055; G06K 9/3241; G06K 2209/05; G06N 3/08; G06N 3/0445; G06N 3/0454; G06N 3/084; G16H 30/20; G16H 50/20
USPC .......................................... 382/128
See application file for complete search history.

(56) References Cited

U.S. PATENT DOCUMENTS

| | | | |
|---|---|---|---|
| 10,136,970 B2 | 11/2018 | Pesach | |
| 10,997,727 B2 | 5/2021 | Xue et al. | |
| 11,013,581 B2 | 5/2021 | Sabina et al. | |
| 11,026,766 B2 | 6/2021 | Chekh et al. | |
| 11,389,131 B2 | 7/2022 | Tuzoff et al. | |
| 2005/0058259 A1* | 3/2005 | Vija | G01T 1/17 378/210 |
| 2006/0223032 A1* | 10/2006 | Fried | A61B 5/0088 433/29 |
| 2007/0127798 A1* | 6/2007 | Chakraborty | G06F 16/94 382/128 |
| 2009/0274998 A1* | 11/2009 | Wong | A61B 5/0088 433/215 |
| 2010/0121658 A1* | 5/2010 | Kaminski | A61C 19/00 715/790 |
| 2012/0189182 A1* | 7/2012 | Liang | A61C 19/00 382/128 |
| 2015/0161786 A1* | 6/2015 | Seifert | G06T 7/149 382/119 |
| 2015/0320320 A1* | 11/2015 | Kopelman | A61B 5/4547 433/215 |
| 2016/0058408 A1* | 3/2016 | Kim | G06T 7/187 382/131 |
| 2016/0117797 A1* | 4/2016 | Li | G06T 7/33 382/128 |
| 2017/0024373 A1* | 1/2017 | Elliot | G06F 16/284 |
| 2018/0116620 A1* | 5/2018 | Chen | A61B 6/5252 |
| 2018/0168781 A1* | 6/2018 | Kopelman | G09B 23/283 |
| 2018/0259608 A1* | 9/2018 | Golden | G06N 3/02 |
| 2018/0357766 A1* | 12/2018 | Van Der Poel | A61B 5/0062 |
| 2019/0090993 A1* | 3/2019 | Engelmohr | A61C 9/0053 |
| 2019/0122411 A1* | 4/2019 | Sachs | G06V 20/647 |
| 2019/0180143 A1* | 6/2019 | Lyu | G06T 1/20 |
| 2019/0180443 A1* | 6/2019 | Xue | G06V 10/44 |
| 2019/0313963 A1* | 10/2019 | Hillen | G06N 3/0454 |
| 2019/0320934 A1* | 10/2019 | Odry | G16H 10/60 |
| 2020/0100724 A1* | 4/2020 | Golay | G16H 70/60 |
| 2020/0146646 A1* | 5/2020 | Tuzoff | A61B 6/563 |

* cited by examiner

AUTOMATED TOOTH LOCALIZATION, ENUMERATION, AND DIAGNOSTIC SYSTEM AND METHOD

BACKGROUND

Field

This invention relates generally to medical diagnostics, and more specifically, to an automated tooth localization, enumeration, and diagnostic system.

Related Art

Modern image generation systems play an important role in disease detection and treatment planning. Few existing systems and methods were discussed as follows. One common method utilized is dental radiography, which provides dental radiographic images that enable the dental professional to identify many conditions that may otherwise go undetected and to see conditions that cannot be identified clinically. Another technology is cone beam computed tomography (CBCT) that allows to view structures in the oral-maxillofacial complex in three dimensions. Hence, cone beam computed tomography technology is most desired over the dental radiography.

However, CBCT includes one or more limitations, such as time consumption and complexity for personnel to become fully acquainted with the imaging software and correctly using digital imaging and communications in medicine (DICOM) data. American Dental Association (ADA) also suggests that the CBCT image should be evaluated by a dentist with appropriate training and education in CBCT interpretation. Further, many dental professionals who incorporate this technology into their practices have not had the training required to interpret data on anatomic areas beyond the maxilla and the mandible. To address the foregoing issues, deep learning has been applied to various medical imaging problems to interpret the generated images, but its use remains limited within the field of dental radiography. Further, most applications only work with 2D X-ray images.

Another existing article entitled "Teeth and jaw 3D reconstruction in stomatology", Proceedings of the International Conference on Medical Information Visualisation—Bio-Medical Visualisation, pp 23-28, 2007, researchers Krsek et al. describe a method dealing with problems of 3D tissue reconstruction in stomatology. In this process, 3D geometry models of teeth and jaw bones were created based on input (computed tomography) CT image data. The input discrete CT data were segmented by a nearly automatic procedure, with manual correction and verification. Creation of segmented tissue 3D geometry models was based on vectorization of input discrete data extended by smoothing and decimation. The actual segmentation operation was primarily based on selecting a threshold of Hounsfield Unit values. However, this method fails to be sufficiently robust for practical use.

Another existing patent number U.S. Pat. No. 8,849,016, entitled "Panoramic image generation from CBCT dental images" to Shoupu Chen et al. discloses a method for forming a panoramic image from a computed tomography image volume, acquires image data elements for one or more computed tomographic volume images of a subject, identifies a subset of the acquired computed tomographic images that contain one or more features of interest and defines, from the subset of the acquired computed tomographic images, a sub-volume having a curved shape that includes one or more of the contained features of interest. The curved shape is unfolded by defining a set of unfold lines wherein each unfold line extends at least between two curved surfaces of the curved shape sub-volume and re-aligning the image data elements within the curved shape sub-volume according to a re-alignment of the unfold lines. One or more views of the unfolded sub-volume are displayed.

Another existing patent application number US20080232539, entitled "Method for the reconstruction of a panoramic image of an object, and a computed tomography scanner implementing said method" to Alessandro Pasini et al. discloses a method for the reconstruction of a panoramic image of the dental arches of a patient, a computer program product, and a computed tomography scanner implementing said method. The method involves acquiring volumetric tomographic data of the object; extracting from the volumetric tomographic data tomographic data corresponding to at least three sections of the object identified by respective mutually parallel planes; determining on each section extracted, a respective trajectory that a profile of the object follows in an area corresponding to said section; determining a first surface transverse to said planes such as to comprise the trajectories, and generating the panoramic image on the basis of a part of the volumetric tomographic data identified as a function of said surface. However, the above references also fail to address the afore discussed problems regarding the cone beam computed tomography technology and image generation system, not to mention an automated anatomical localization and pathology detection/classification means.

Therefore, there is a need for an automated parsing pipeline system and method for anatomical localization and condition classification, with minimal image analysis training and visual ambiguities. Furthermore, there is a need for applying deep learning models for constructing panoramas from CBCT images that emphasize Elements of Interest (EoI) for more defined and actionable imaging. Going a step further, there is a need for further processing these EoI focused panoramas using deep learning methods to generate accurate 3D teeth segmentation masks with localization.

Furthermore, extant annotation tools configured for a full mouth set of x-rays (FMX) or panoramic radiographs enable overlaying images with descriptive information for centralized storage and efficient querying support, allowing practitioners and proxy to construct complex queries to find meaningful, related cases efficiently later. The extant annotation tools do not support localizing and enumerating teeth in the images using neural networks, and certainly, do not support sorting images into a full mount table with neural network-mediated classification of a tooth condition with diagnostic value. Therefore, there is void in the art for an automated localization, numeration, and diagnostic system and method for FMX and panoramic images for improved dental health outcomes.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. Embodiments disclosed include an automated parsing pipeline system and method for anatomical localization and condition classification. Embodiments disclosed also include for a method and system for constructing a panorama with elements of interest (EoI) emphasized of a teeth arch or any point of interest in a oral-maxillofacial complex. Further embodiments disclosed include for an automated system and method for localizing, enumerating, and diagnosing a tooth/tooth condition from a FMX/Panoramic image for improved dental outcomes.

In an embodiment, the system comprises an input event source, a memory unit in communication with the input event source, a processor in communication with the memory unit, a volumetric image processor in communication with the processor, a voxel parsing engine in communication with the volumetric image processor and a localizing layer in communication with the voxel parsing engine. In one embodiment, the memory unit is a non-transitory storage element storing encoded information. In one embodiment, at least one volumetric image data is received from the input event source by the volumetric image processor. In one embodiment, the input event source is a radio-image gathering source.

The processor is configured to parse the at least one received volumetric image data into at least a single image frame field of view by the volumetric image processor. The processor is further configured to localize anatomical structures residing in the at least single field of view by assigning at least one of a pixel and voxel a distinct anatomical structure by the voxel parsing engine. In one embodiment, the single image frame field of view is pre-processed for localization, which involves rescaling using linear interpolation. The pre-processing involves use of any one of a normalization schemes to account for variations in image value intensity depending on at least one of an input or output of volumetric image. In one embodiment, localization is achieved using any one of a fully convolutional network (FCN) or plain classification convolutional neural network (CNN).

The processor is further configured to select at least one of all pixels and voxels (p/v) belonging to the localized anatomical structure by finding a minimal bounding rectangle around the p/v and the surrounding region for cropping as a defined anatomical structure by the localization layer. The bounding rectangle extends equally in all directions to capture the tooth and surrounding context. In one embodiment, the automated parsing pipeline system further comprises a detection module. The processor is configured to detect or classify the conditions for each defined anatomical structure within the cropped image by a detection module or classification layer. In one embodiment, the classification is achieved using any one of a fully convolutional network or plain classification convolutional neural network (FCN/CNN).

In another embodiment, an automated parsing pipeline method for anatomical localization and condition classification is disclosed. At one step, at least one volumetric image data is received from an input event source by a volumetric image processor. At another step, the received volumetric image data is parsed into at least a single image frame field of view by the volumetric image processor. At another step, the single image frame field of view is pre-processed by controlling image intensity value by the volumetric image processor. At another step, the anatomical structure residing in the single pre-processed field of view is localized by assigning each p/v a distinct anatomical structure ID by the voxel parsing engine. At another step, all p/v belonging to the localized anatomical structure is selected by finding a minimal bounding rectangle around the voxels and the surrounding region for cropping as a defined anatomical structure by the localization layer. In another embodiment, the method includes a step of, classifying the conditions for each defined anatomical structure within the cropped image by the classification layer.

Further embodiments disclosed include a method and system for constructing a panorama with elements of interest (EoI) emphasized of a teeth arch or any point of interest in an oral-maxillofacial complex. Other embodiments of this aspect also include for any various deep learning models or modules for processing any one of the steps in the construction of 2D or 3D or 2D/3D-fused teeth segmentation masks with localization. It should be appreciated that any point of interest in the oral-maxillofacial complex may be translated into the EoI-focused panorama/mask for higher-defined actionable imaging.

Further embodiments disclose for a system and method for localizing, annotating, and diagnosing a tooth/tooth condition from a FMX or panoramic image. In one embodiment, the system may comprise an image processor; a localization layer; a sorting engine; a processor; a non-transitory storage element coupled to the processor; encoded instructions stored in the non-transitory storage element, wherein the encoded instructions when implemented by the processor, configure the system to: receive a series of at least one of an intra-oral or panoramic images constituting a full mouth series from a radio-image gathering or digital capturing source for processing by the image processor; parse the series of images into at least a single image frame field of view by said image processor; localize and enumerate at least one tooth residing in the at least single image frame field of view by assigning each pixel a distinct tooth structure by selecting all pixels belonging to the localized tooth structure by finding a minimal bounding rectangle around said pixels and the surrounding region for cropping as a defined enumerated tooth structure image by the localization layer; and sort images using the defined enumerated tooth structure images to fill an FMX mounting table by the sorting engine.

In another embodiment, the system may further comprise an image processor; a localization layer; a diagnostic module or classification layer; a processor; a non-transitory storage element coupled to the processor; encoded instructions stored in the non-transitory storage element, wherein the encoded instructions when implemented by the processor, configure the system to: receive a series of at least one of an intra-oral or panoramic images constituting a full mouth series from a radio-image gathering or digital capturing source for processing by the image processor; localize and enumerate at least one tooth residing in at least single image frame field of view by assigning each pixel a distinct tooth structure by selecting all pixels belonging to the localized tooth structure by finding a minimal bounding rectangle around said pixels and the surrounding region for cropping as a defined enumerated tooth structure image by the localization layer; and detect conditions for each defined enumerated tooth structure within a cropped image, wherein conditions are detected by the classification layer, wherein the classification layer at least one of detects or segments conditions and pathologies on at least one of the enumerated tooth structures within the cropped image.

In yet another embodiment, a method is disclosed, entailing the steps involved for localizing, annotating, and optionally, diagnosing a tooth condition carried out by the automated pipeline or system. Generally, the steps are: receiving a series of at least one of an intra-oral or panoramic images constituting a full mouth series from a radio-image gathering or digital capturing source for processing; localizing and enumerating at least one tooth residing in at least single image frame field of view by assigning each pixel a distinct tooth structure by selecting all pixels belonging to the localized tooth structure by finding a minimal bounding rectangle around said pixels and the surrounding region for cropping as a defined enumerated tooth structure image; and (optionally) sorting images using the defined enumerated tooth structure images to fill an FMX mounting table.

Furthermore, the method may optionally further comprise the step of detecting conditions for each defined enumerated tooth structure within a cropped image, wherein conditions are detected by at least one of detecting or segmenting conditions and pathologies on at least one of the enumerated tooth structures within the cropped image. Other embodiments of this aspect include corresponding computer systems, apparatus, and computer programs recorded on one or more computer storage devices, each configured to perform the actions of the methods.

DETAILED DESCRIPTION

Specific embodiments of the invention will now be described in detail with reference to the accompanying FIGS. 1A-7. In the following detailed description of embodiments of the invention, numerous specific details are set forth in order to provide a more thorough understanding of the invention. In other instances, well-known features have not been described in detail to avoid obscuring the invention. Embodiments disclosed include an automated parsing pipeline system and method for anatomical localization and condition classification.

Figure 1A:
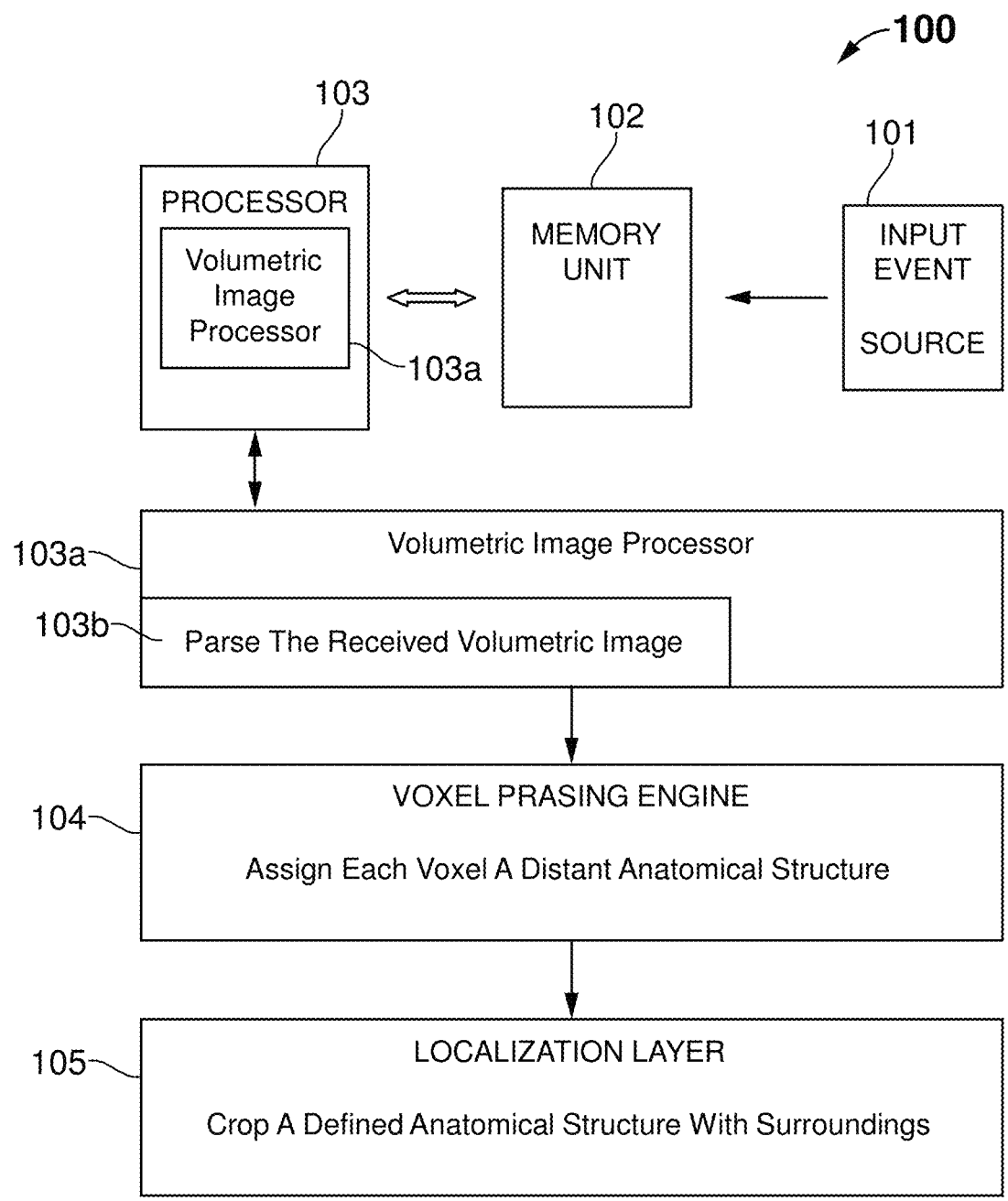
FIG. 1A illustrates in a block diagram, an automated parsing pipeline system for anatomical localization and condition classification, according to an embodiment.

FIG. 1A illustrates a block diagram 100 of the system comprising an input event source 101, a memory unit 102 in communication with the input event source 101, a processor 103 in communication with the memory unit 102, a volumetric image processor 103a in communication with the processor 103, a voxel parsing engine 104 in communication with the volumetric image processor 103a and a localizing layer 105 in communication with the voxel parsing engine 104. In an embodiment, the memory unit 102 is a non-transitory storage element storing encoded information. The encoded instructions when implemented by the processor 103, configure the automated pipeline system to localize an anatomical structure and classify the condition of the localized anatomical structure.

In one embodiment, an input data is provided via the input event source 101. In one embodiment, the input data is a volumetric image data and the input event source 101 is a radio-image gathering source. In one embodiment, the input data is a 2-Dimensional (2D) image data. In another embodiment, the input data is a 3-Dimensional (3D) image data. The volumetric image processor 103a is configured to receive the volumetric image data from the radio-image gathering source. Initially, the volumetric image data is pre-processed, which involves conversion of 3-D pixel array into an array of Hounsfield Unit (HU) radio intensity measurements.

The processor 103 is further configured to parse at least one received image or volumetric image data 103b (i/v.i)

into at least a single image frame field of view by the volumetric image processor. The processor 103 is further configured to localize anatomical structures residing in the single image frame field of view by assigning at least one of each a pixel or voxel (p/v) a distinct anatomical structure by the voxel parsing engine 104. In one embodiment, the single image frame field of view is pre-processed for localization, which involves rescaling using linear interpolation. The pre-processing involves use of any one of a normalization schemes to account for variations in image value intensity depending on at least one of an input or output of an image or volumetric image (i/v.i). In one embodiment, localization is achieved using any one of fully convolutional network or plain classification convolutional neural network (FCN/CNN), such as a V-Net-based fully convolutional neural network. In one embodiment, the V-Net is a 3D generalization of UNet.

The processor 103 is further configured to select all p/v belonging to the localized anatomical structure by finding a minimal bounding rectangle around the p/v and the surrounding region for cropping as a defined anatomical structure by the localization layer. The bounding rectangle extends equally in all directions to capture the tooth and surrounding context. In one embodiment, the bounding rectangle may extend 8-15 mm in all directions to capture the tooth and surrounding context.

Figure 1B:
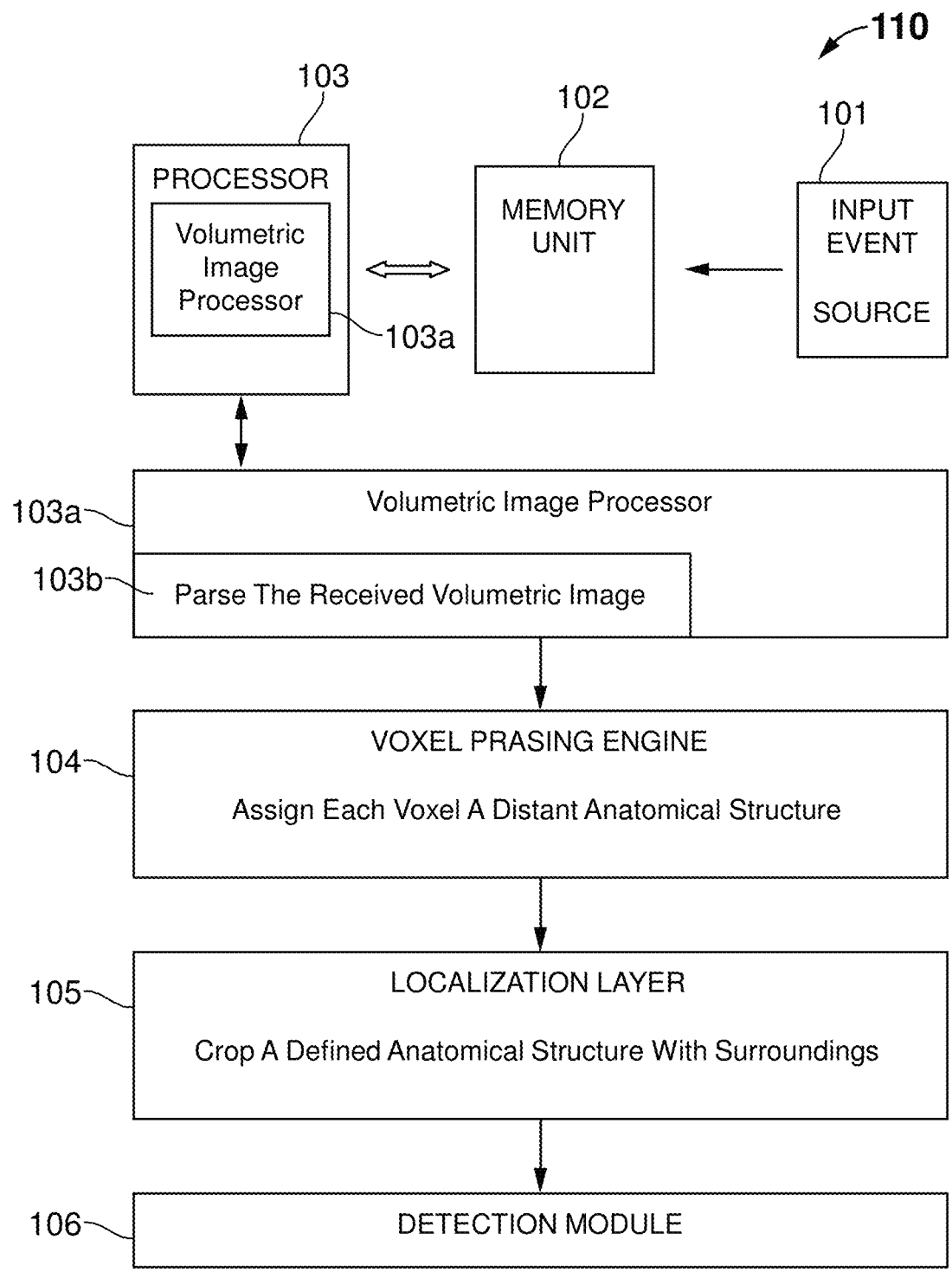
FIG. 1B illustrates in a block diagram, an automated parsing pipeline system for anatomical localization and condition classification, according to another embodiment.

FIG. 1B illustrates in a block diagram 110, an automated parsing pipeline system for anatomical localization and condition classification, according to another embodiment. The automated parsing pipeline system further comprises a detection module 106. The processor 103 is configured to detect or classify the conditions for each defined anatomical structure within the cropped image by a detection module or classification layer 106. In one embodiment, the classification is achieved using any one of a FCN/CNN, such as a DenseNet 3-D convolutional neural network.

In one embodiment, the localization layer 105 includes 33 class semantic segmentation in 3D. In one embodiment, the system is configured to classify each p/v as one of 32 teeth or background and resulting segmentation assigns each p/v to one of 33 classes. In another embodiment, the system is configured to classify each p/v as either tooth or other anatomical structure of interest. In case of localizing only teeth, the classification includes, but not limited to, 2 classes. Then individual instances of every class (teeth) could be split, e.g. by separately predicting a boundary between them. In some embodiments, the anatomical structure being localized, includes, but not limited to, teeth, upper and lower jaw bone, sinuses, lower jaw canal and joint.

In one embodiment, the system utilizes fully-convolutional network. In another embodiment, the system works on downscaled images (typically from 0.1-0.2 mm i/v.i resolution to 1.0 mm resolution) and grayscale (1-channel) image (say, 1×100×100×100-dimensional tensor). In yet another embodiment, the system outputs 33-channel image (say, 33×100×100×100-dimensional tensor) that is interpreted as a probability distribution for non-tooth vs. each of 32 possible (for adult human) teeth, for every p/v.

In an alternative embodiment, the system provides 2-class segmentation, which includes labelling or classification, if the localization comprises tooth or not. The system additionally outputs assignment of each tooth p/v to a separate "tooth instance".

In one embodiment, the system comprises FCN/CNN (such as VNet) predicting multiple "energy levels", which are later used to find boundaries. In another embodiment, a recurrent neural network could be used for step by step prediction of tooth, and keep track of the teeth that were outputted a step before. In yet another embodiment, Mask-RCNN generalized to 3D could be used by the system. In yet another embodiment, the system could take multiple crops from 3D image in original resolution, perform instance segmentation, and then join crops to form mask for all original image. In another embodiment, the system could apply either segmentation or object detection in 2D, to segment axial slices. This would allow to process images in original resolution (albeit in 2D instead of 3D) and then infer 3D shape from 2D segmentation.

In one embodiment, the system could be implemented utilizing descriptor learning in the multitask learning framework i.e., a single network learning to output predictions for multiple dental conditions. This could be achieved by balancing loss between tasks to make sure every class of every task have approximately same impact on the learning. The loss is balanced by maintaining a running average gradient that network receives from every class*task and normalizing it. Alternatively, descriptor learning could be achieved by teaching network on batches consisting data about a single condition (task) and sample examples into these batches in such a way that all classes will have same number of examples in batch (which is generally not possible in multitask setup). Further, standard data augmentation could be applied to 3D tooth images to perform scale, crop, rotation, vertical flips. Then, combining all augmentations and final image resize to target dimensions in a single affine transform and apply all at once.

Advantageously, in some embodiments, to accumulate positive cases faster, a weak model could be trained and ran for all of the unlabeled data. From resulting predictions, teeth model that yield high scores on some rare pathology of interest are selected. Then the teeth are sent to be labelled and added to the dataset (both positive and negative labels). This allows to quickly and cost-efficiently build up a more balanced dataset for rare pathologies.

In some embodiments, the system could use coarse segmentation mask from localizer as an input instead of tooth image. In some embodiments, the descriptor could be trained to output fine segmentation mask from some of the intermediate layers. In some embodiments, the descriptor could be trained to predict tooth number.

As an alternative to multitask learning approach, "one network per condition" could be employed, i.e. models for different conditions are completely separate models that share no parameters. Another alternative is to have a small shared base network and use separate subnetworks connected to this base network, responsible for specific conditions/diagnoses.

Figure 2A:
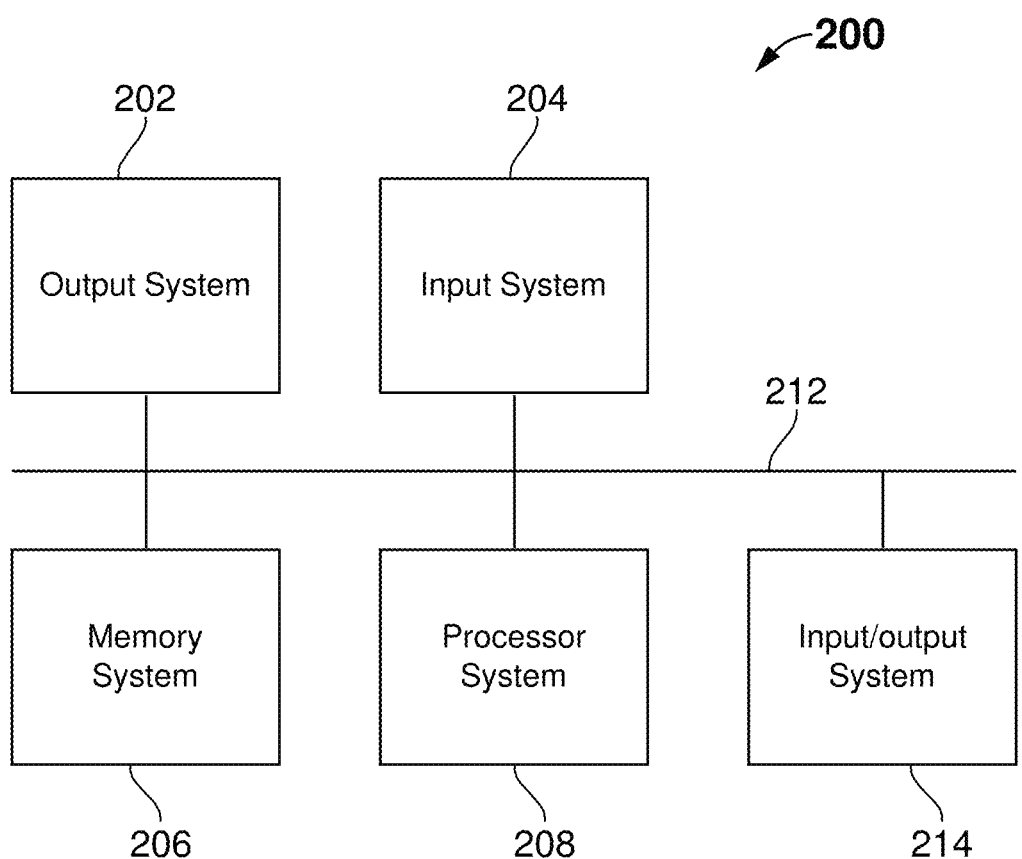
FIG. 2A illustrates in a block diagram, an automated parsing pipeline system for anatomical localization and condition classification according to yet another embodiment.
Figure 2B:
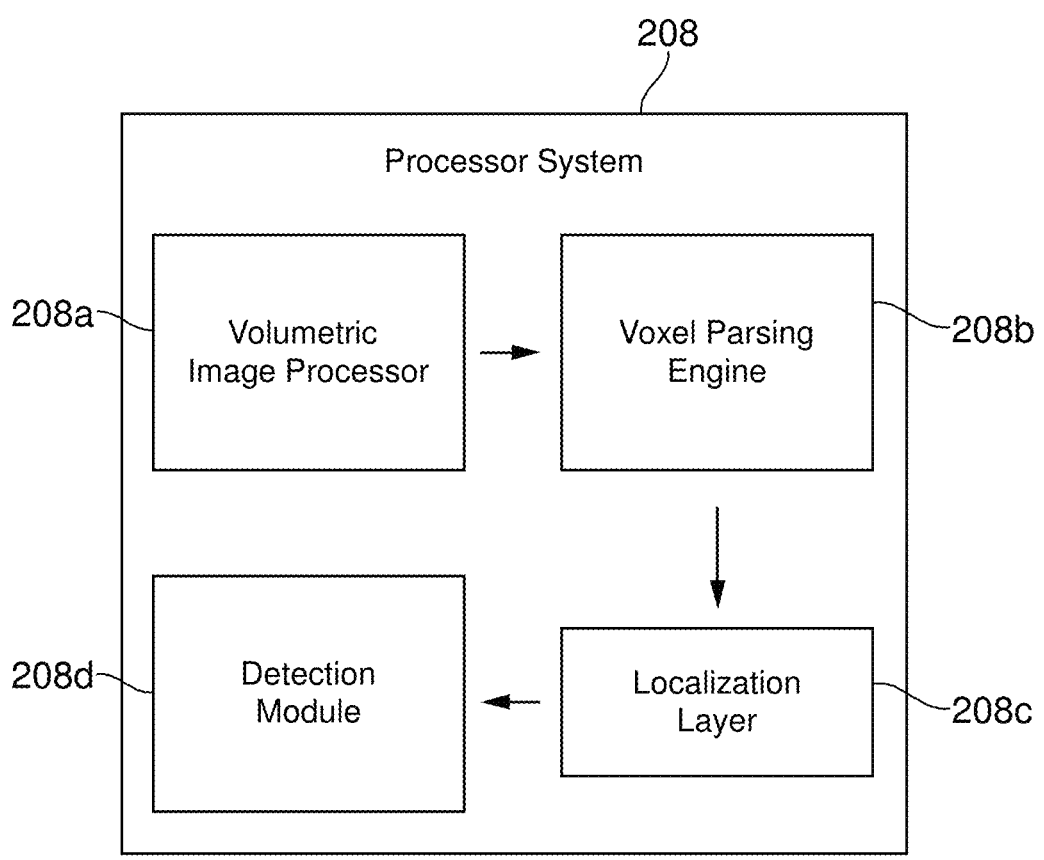
FIG. 2B illustrates in a block diagram, a processor system according to an embodiment.

FIG. 2A illustrates in a block diagram 200, an automated parsing pipeline system for anatomical localization and condition classification according to yet another embodiment. In an embodiment, the system comprises an input system 204, an output system 202, a memory system or unit 206, a processor system 208, an input/output system 214 and an interface 212. Referring to FIG. 2B, the processor system 208 comprises a volumetric image processor 208a, a voxel parsing engine 208b in communication with the volumetric image processor 208a, a localization layer 208c in communication with the voxel parsing engine 208 and a detection module 208d in communication with the localization module 208c. The processor 208 is configured to receive at least one i/v.i via an input system 202. At least one received i/v.i, which may be comprised of a 2-D or 3-D image. The pixel array is pre-processed to convert into an array of Hounsfield Unit (HU) radio intensity measurements. Then, the processor 208 is configured to parse the received i/v.i into at least a single image frame field of view by the said volumetric image processor 208a.

The anatomical structures residing in the at least single field of view is localized by assigning each p/v a distinct anatomical structure by the voxel parsing engine 208b. The processor 208 is configured to select all p/v belonging to the localized anatomical structure by finding a minimal bounding rectangle around the p/v and the surrounding region for cropping as a defined anatomical structure by the localization layer 208c. Then, the conditions for each defined anatomical structure within the cropped image is classified by a detection module or classification layer 208d.

Figure 3A:
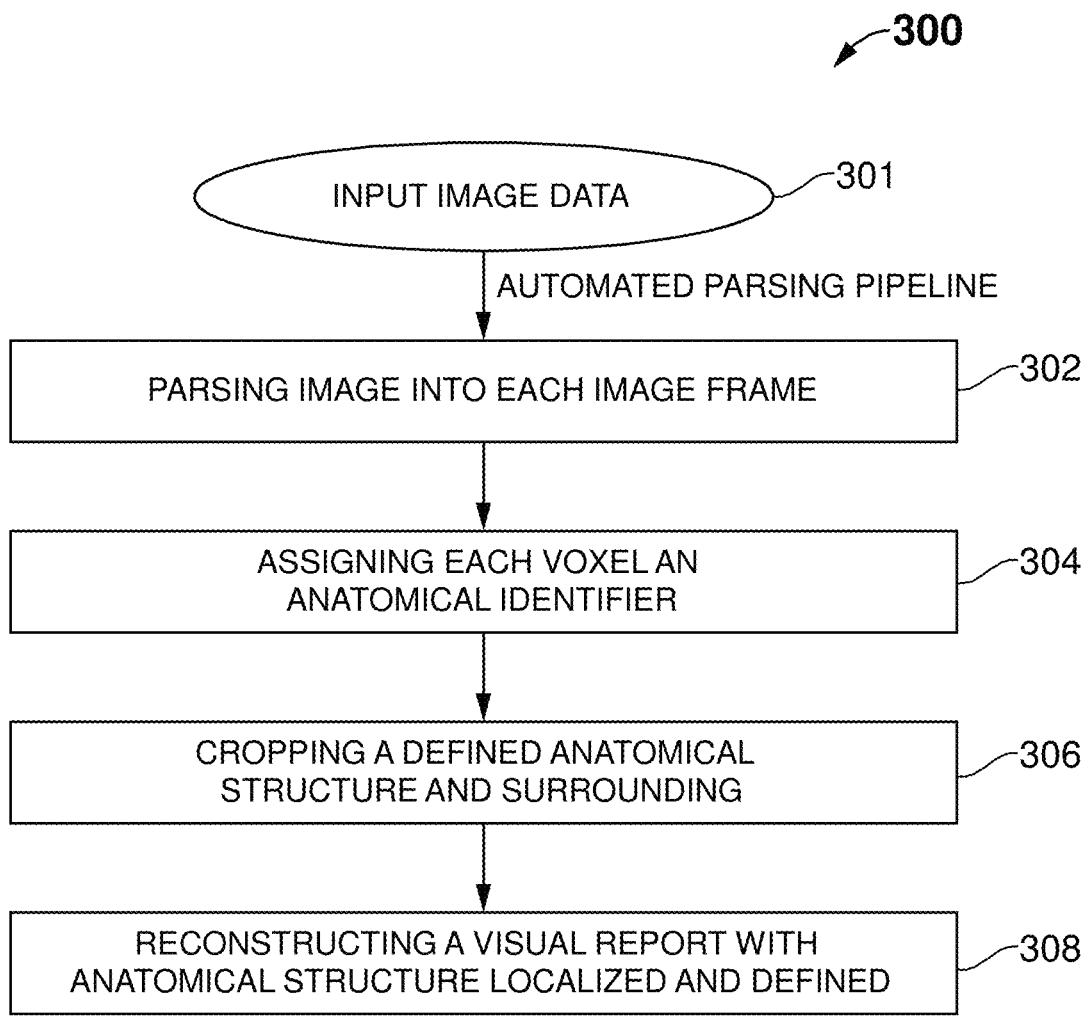
FIG. 3A. illustrates in a flow diagram, an automated parsing pipeline method for anatomical localization and condition classification, according to an embodiment.

FIG. 3A illustrates in a flow diagram 300, an automated parsing pipeline method for anatomical localization and condition classification, according to an embodiment. At step 301, an input image data is received. In one embodiment, the image data is a i/v.i. At step 302, the received i/v.i is parsed into at least a single image frame field of view. The parsed i/v.i is pre-processed by controlling image intensity value.

At step 304, a tooth or anatomical structure inside the pre-processed and parsed i/v.i is localized and identified by tooth number. At step 306, the identified tooth and surrounding context within the localized i/v.i are extracted. At step 308, a visual report is reconstructed with localized and defined anatomical structure. In some embodiments, the visual reports include, but not limited to, an endodontic report (with focus on tooth's root/canal system and its treatment state), an implantation report (with focus on the area where the tooth is missing), and a dystopic tooth report for tooth extraction (with focus on the area of dystopic/impacted teeth).

Figure 3B:
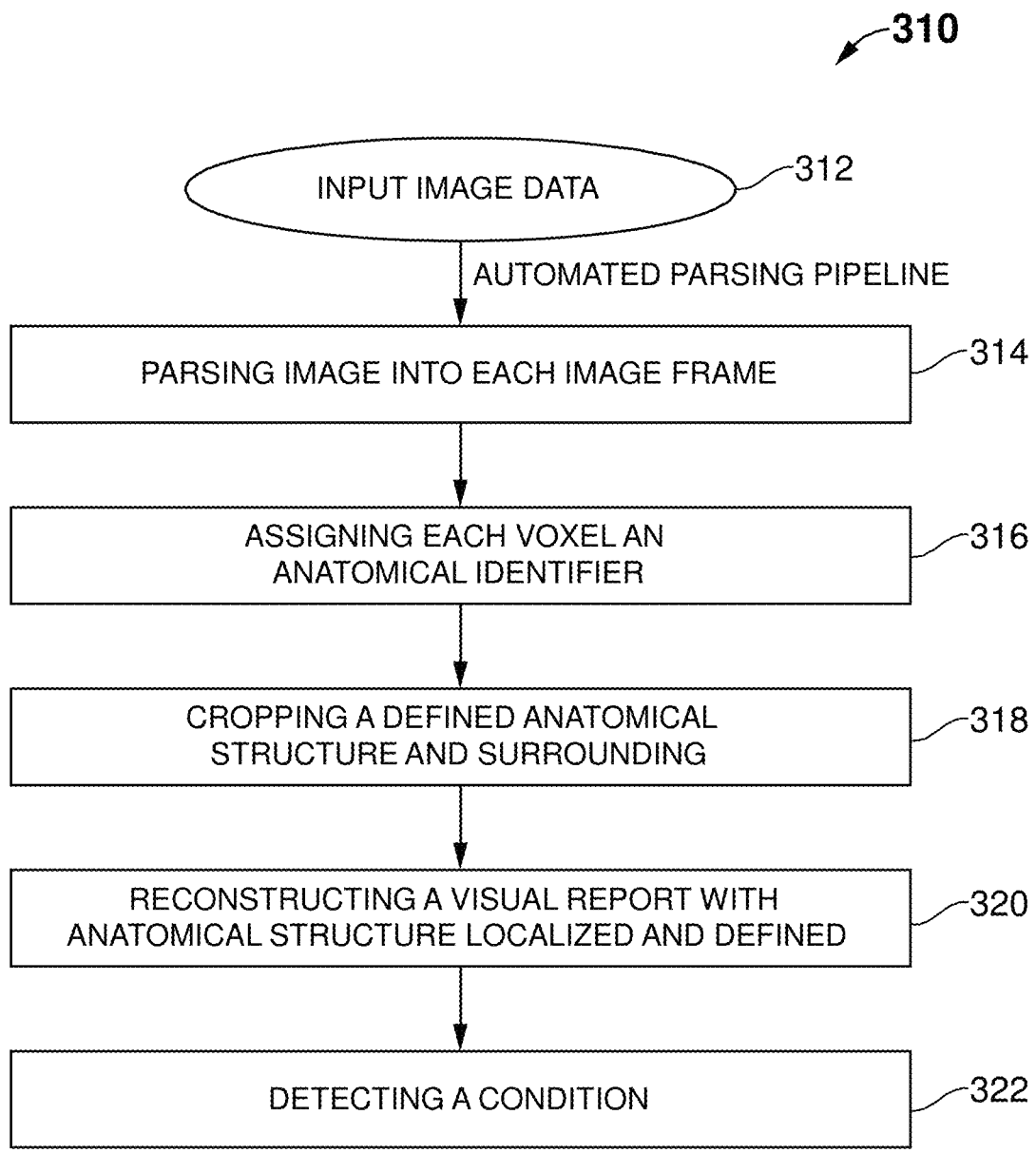
FIG. 3B illustrates in a flow diagram, an automated parsing pipeline method for anatomical localization and condition classification, according to another embodiment.

FIG. 3B illustrates in a flow diagram 310, an automated parsing pipeline method for anatomical localization and condition classification, according to another embodiment. At step 312, at least one i/v.i is received from a radio-image gathering source by a volumetric image processor.

At step 314, the received i/v.i is parsed into at least a single image frame field of view by the volumetric image processor. At least single image frame field of view is pre-processed by controlling image intensity value by the volumetric image processor. At step 316, an anatomical structure residing in the at least single pre-processed field of view is localized by assigning each p/v a distinct anatomical structure ID by the voxel parsing engine. At step 318, all p/v belonging to the localized anatomical structure is selected by finding a minimal bounding rectangle around the p/v and the surrounding region for cropping as a defined anatomical structure by the localization layer. At step 320, a visual report is reconstructed with defined and localized anatomical structure. At step 322, conditions for each defined anatomical structure is classified within the cropped image by the classification layer.

Figure 4:
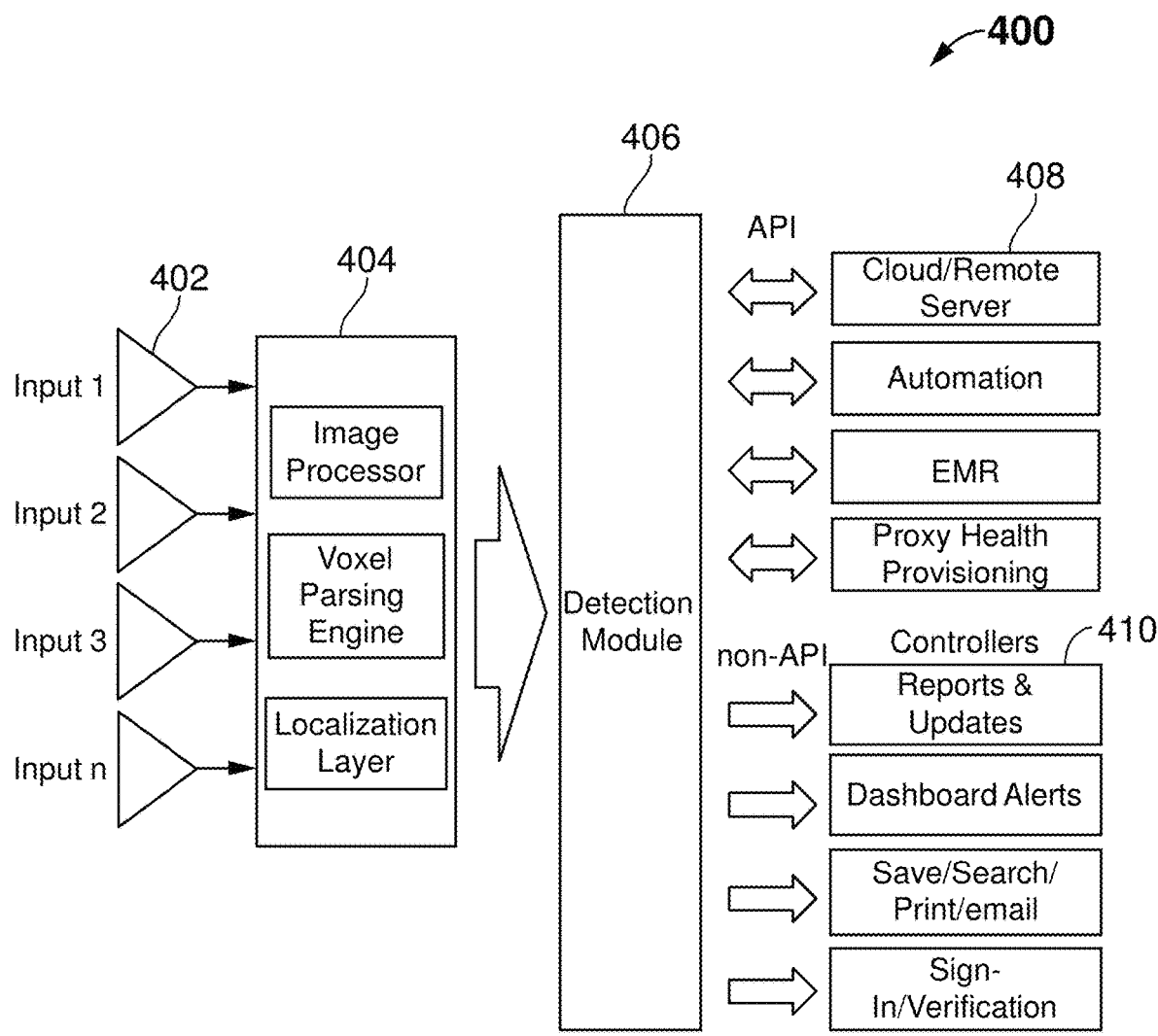
FIG. 4 illustrates in a block diagram, the automated parsing pipeline architecture according to an embodiment.

FIG. 4 illustrates in a block diagram 400, the automated parsing pipeline architecture according to an embodiment. According to an embodiment, the system is configured to receive input image data from a plurality of capturing devices, or input event sources 402. A processor 404 including an image processor, a voxel parsing engine and a localization layer. The image processor is configured to parse image into each image frame and preprocess the parsed image. The voxel parsing engine is configured to configured to localize an anatomical structure residing in the at least single pre-processed field of view by assigning each p/v a distinct anatomical structure ID. The localization layer is configured to select all p/v belonging to the localized anatomical structure by finding a minimal bounding rectangle around the p/v and the surrounding region for cropping as a defined anatomical structure. The detection module 406 is configured to detect the condition of the defined anatomical structure. The detected condition could be sent to the cloud/remote server, for automation, to EMR and to proxy health provisioning 408. In another embodiment, detected condition could be sent to controllers 410. The controllers 410 includes reports and updates, dashboard alerts, export option or store option to save, search, print or email and sign-in/verification unit.

Figure 5:
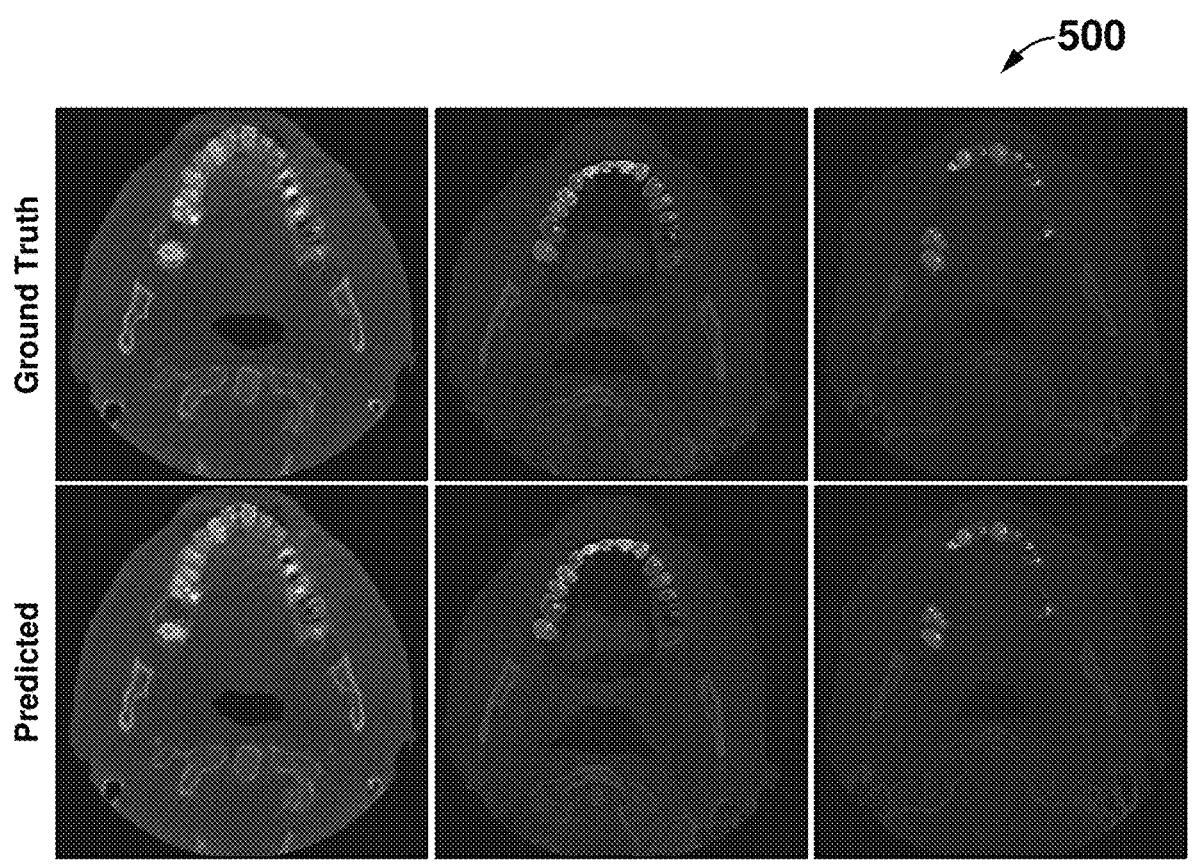
FIG. 5 illustrates in a screenshot, an example of ground truth and predicted masks in an embodiment of the present invention.

Referring to FIG. 5, an example screenshot 500 of tooth localization done by the present system, is illustrated. This figure shows examples of teeth segmentation at axial slices of 3D tensor.

Problem: Formulating the problem of tooth localization as a 33-class semantic segmentation. Therefore, each of the 32 teeth and the background are interpreted as separate classes.

Model: A V-Net-based fully convolutional network is used. V-Net is a 6-level deep, with widths of 32; 64; 128; 256; 512; and 1024. The final layer has an output width of 33, interpreted as a softmax distribution over each voxel, assigning it to either the background or one of 32 teeth. Each block contains 3*3*3 convolutions with padding of 1 and stride of 1, followed by ReLU non-linear activations and a dropout with 0:1 rate. Instance normalization before each convolution is used. Batch normalization was not suitable in this case, as long as there is only one example in batch (GPU memory limits); therefore, batch statistics are not determined.

Different architecture modifications were tried during the research stage. For example, an architecture with 64; 64; 128; 128; 256; 256 units per layer leads to the vanishing gradient flow and, thus, no training. On the other hand, reducing architecture layers to the first three (three down and three up) gives a comparable result to the proposed model, though the final loss remains higher.

Loss function: Let R be the ground truth segmentation with voxel values $r_i$ (0 or 1 for each class), and P the predicted probabilistic map for each class with voxel values $p_i$. As a loss function we use soft negative multi-class Jaccard similarity, that can be defined as:

$$\text{Jaccard Multi class Loss} = 1 - \frac{1}{N}\sum_{i=0}^{N}\frac{p_i r_i + \epsilon}{p_i + r_i - p_i r_i + \epsilon'}$$

where N is the number of classes, which in our case is 32, and $\epsilon$ is a loss function stability coefficient that helps to avoid a numerical issue of dividing by zero. Then the model is trained to convergence using an Adam optimizer with learning rate of 1e-4 and weight decay 1e-8. A batch size of 1 is used due to the large memory requirements of using volumetric data and models. The training is stopped after 200 epochs and the latest checkpoint is used (validation loss does not increase after reaching the convergence plateau).

Results: The localization model is able to achieve a loss value of 0:28 on a test set. The background class loss is 0:0027, which means the model is a capable 2-way "tooth/not a tooth" segmentor. The localization intersection over union (IoU) between the tooth's ground truth volumetric bounding box and the model-predicted bounding box is also defined. In the case where a tooth is missing from ground truth and the model predicted any positive p/v (i.e. the ground truth bounding box is not defined), localization IoU is set to 0. In the case where a tooth is missing from ground truth and the model did not predict any positive p/v for it, localization IoU is set to 1. For a human-interpretable metric, tooth localization accuracy which is a percent of teeth is used that have a localization IoU greater than 0:3 by definition. The relatively low threshold value of 0:3 was decided from the manual observation that even low localization IoU values are enough to approximately localize teeth for the downstream processing. The localization model achieved a value of 0:963 IoU metric on the test set, which, on average, equates to the incorrect localization of 1 of 32 teeth.

Figures 6A, 6B, 6C:
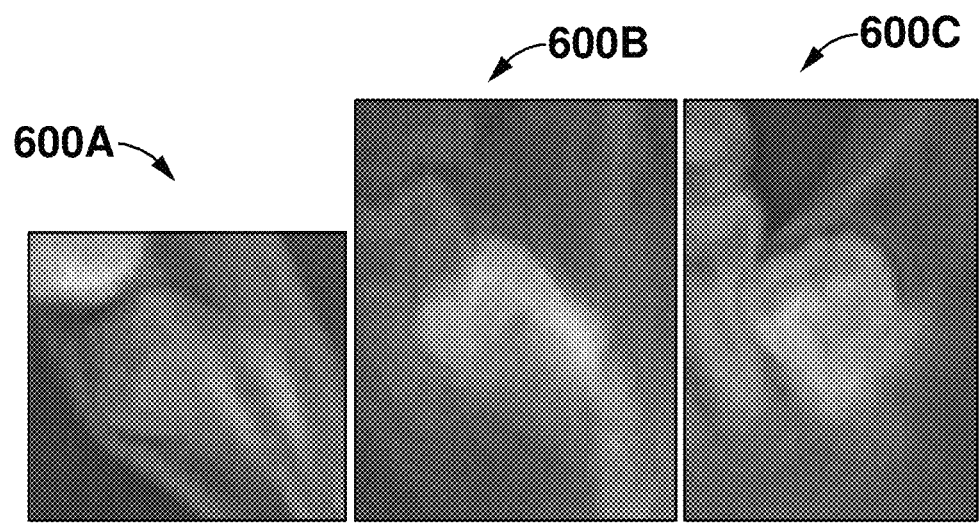
FIG. 6A illustrates in a screenshot, the extraction of anatomical structure by the localization model of the system in an embodiment of the present invention.
FIG. 6B illustrates in a screenshot, the extraction of anatomical structure by the localization model of the system in an embodiment of the present invention.
FIG. 6C illustrates in a screenshot, the extraction of anatomical structure by the localization model of the system in an embodiment of the present invention.

Referring to FIGS. 6A-6C, an example screenshot (600A, 600B, 600B) of tooth sub-volume extraction done by the present system, illustrated.

In order to focus the downstream classification model on describing a specific tooth of interest, the tooth and its surroundings is extracted from the original study as a rectangular volumetric region, centered on the tooth. In order to get the coordinates of the tooth, the upstream segmentation mask is used. The predicted volumetric binary mask of each tooth is preprocessed by applying erosion, dilation, and then selecting the largest connected component. A minimum bounding rectangle is found around the predicted volumetric mask. Then, the bounding box is extended by 15 mm vertically and 8 mm horizontally (equally in all directions) to capture the tooth and surrounding region (tooth context) and to correct possibly weak localizer performance. In other embodiments, the minimum bounding box may be any length in either direction to optimally capture tooth context. Finally, a corresponding sub-volume is extracted from the original clipped image, rescale it to 643 and pass it on to the classifier. An example of

|  | Artificial crowns | Filling canals | Filling | Impacted tooth | Implant | Missing |
|---|---|---|---|---|---|---|
| ROCAUC | 0.941 | 0.95 | 0.892 | 0.931 | 0.979 | 0.946 |
| Condition frequency | 0.092 | 0.129 | 0.215 | 0.018 | 0.015 | 0.145 | a sub-volume bounding box is presented in FIGS. 6A-6C.

Figure 7:
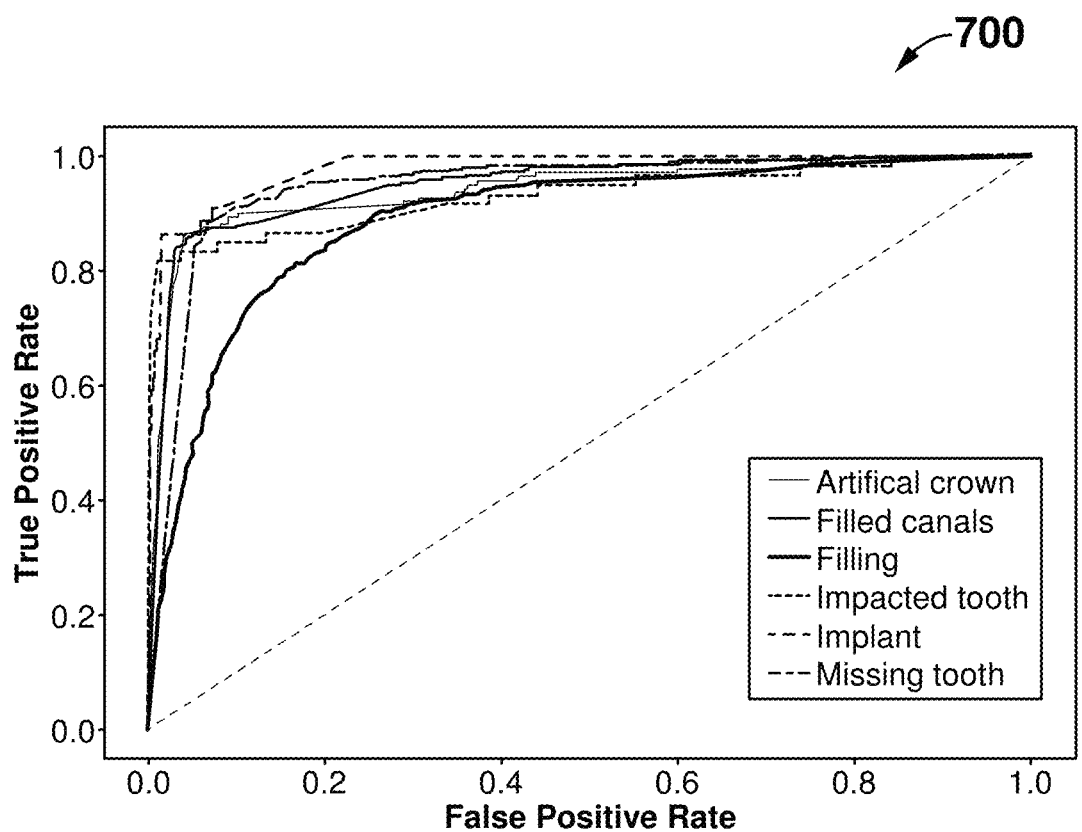
FIG. 7 illustrates in a graph, receiver operating characteristic (ROC) curve of a predicted tooth condition in an embodiment of the present invention.

Referring to FIG. 7, a receiver operating characteristic (ROC) curve 700 of a predicted tooth condition is illustrated.

Model: The classification model has a DenseNet architecture. The only difference between the original and implementation of DenseNet by the present invention is a replacement of the 2D convolution layers with 3D ones. 4 dense blocks of 6 layers is used, with a growth rate of 48, and a compression factor of 0:5. After passing the 643 input through 4 dense blocks followed by down-sampling transitions, the resulting feature map is 548×2×2×2. This feature map is flattened and passed through a final linear layer that outputs 6 logits—each for a type of abnormality.

Loss function: Since tooth conditions are not mutually exclusive, binary cross entropy is used as a loss. To handle class imbalance, weight each condition loss inversely proportional to its frequency (positive rate) in the training set. Suppose that Fi is the frequency of condition i, pi is its predicted probability (sigmoid on output of network) and ti is ground truth. Then: Li=(1=Fi). ti .log pi+Fi. (1–ti) .log (1–pi) is the loss function for condition i. The final example loss is taken as an average of the 6 condition losses.

Results: The classification model achieved average area under the receiver operating characteristic curve (ROC AUC) of 0:94 across the 6 conditions. Per-condition scores are presented in above table. Receiver operating characteristic (ROC) curves 700 of the 6 predicted conditions are illustrated in FIG. 7.

Figure 8:
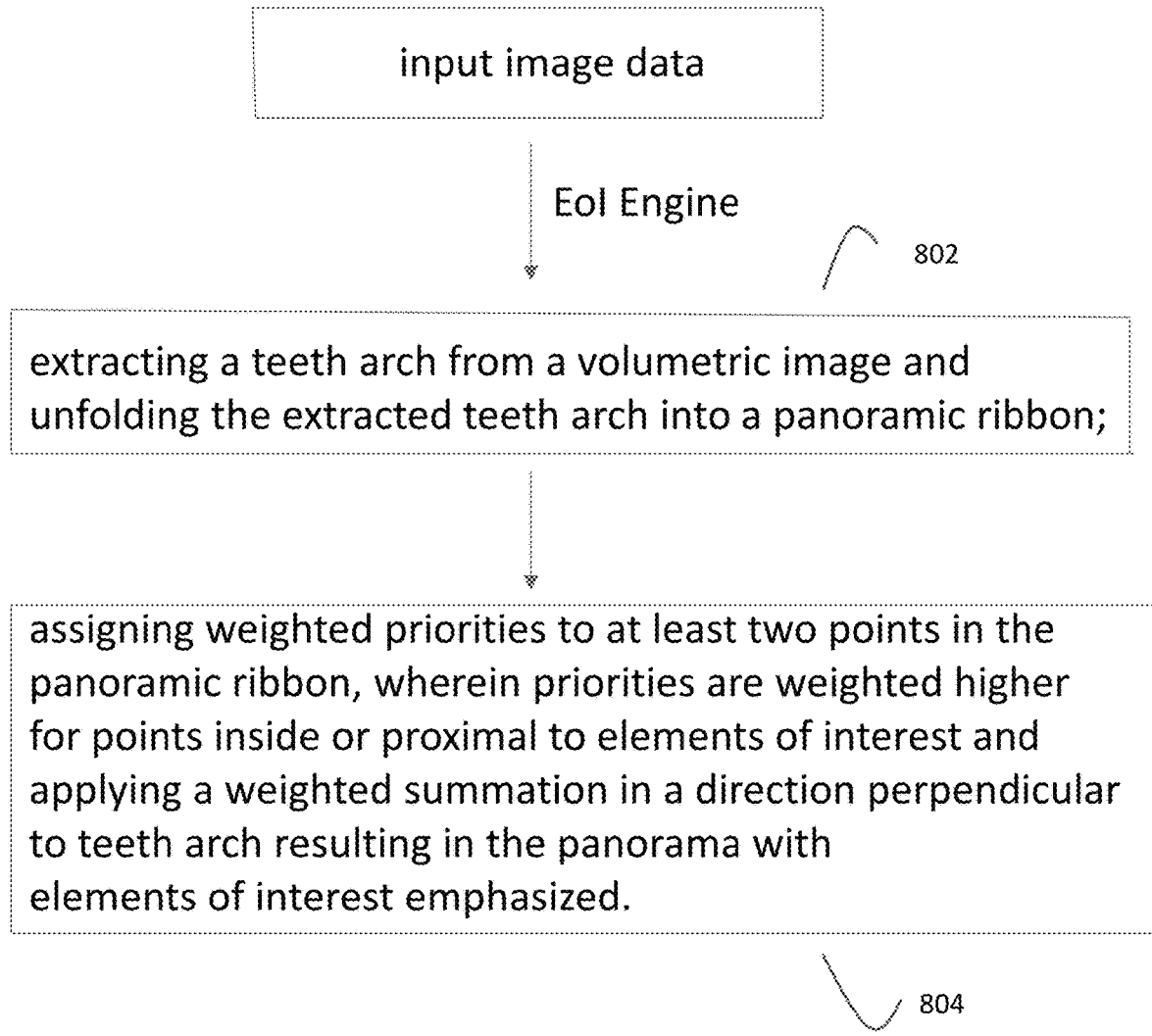
FIG. 8 illustrates a method flow diagram of exemplary steps in the construction of an EoI-focused panorama in accordance with an aspect of the invention.

FIG. 8 illustrates a method flow diagram of exemplary steps in the construction of an EoI-focused panorama in accordance with an aspect of the invention. It is to be understood that references to anatomical structures may also assume image or image data corresponding to the structure. For instance, extracting a teeth arch translates to extracting the portion of the image wherein the teeth arch resides, and not the literal anatomical structure. FIG. 8 generally illustrates a method of steps for constructing a 2D panoramic image from a 3D CBCT study. More specifically, in one embodiment, disclosed is a method for constructing a panorama of teeth arch with elements of interest emphasized. In a preferred embodiment, the method comprises the step of: (1) extracting a teeth arch from a volumetric image and unfolding the extracted teeth arch into a panoramic ribbon 802; and step (2) assigning weighted priorities to at least two points in the panoramic ribbon, wherein priorities are weighted higher for points inside or proximal to elements of interest (EoI) and applying a weighted summation in a direction perpendicular to teeth arch resulting in the panorama with EoI emphasized 804.

The construction of the EoI-focused panorama of an oral complex (or more specifically, a teeth arch) is generally achieved in two steps according to one embodiment: The first step concludes in voxel coordinates operations, such as extracting teeth arch and unfolding a study image into 3D panoramic ribbon (curved sub-volume that passes along the teeth arch). Teeth arch is extracted using segmentations of teeth and anatomy, mandible and mandibular canals in particular. Anatomy segmentation may also required to maintain stable extraction in case of missing teeth and to ensure that TMJs and canals are visualized in panorama. Then, construct a transformation grid that allows the arch to unfold in straight line, resulting in a panoramic ribbon. In one embodiment, the transformation grid is a calculation of the coordinates according to the coordinates of the original volumetric image. Once unfolded, in one embodiment, the resulting image is virtually tilted in sagittal plane for frontal teeth apexes to take the most perceptible position. Tilting of the ribbon to maximize perceptibility of a frontal teeth apex is done by calculating the angles of frontal section tilt for both sections, applying the transformations according to the calculated tilt during the process of calculating of the coordinates of a transformation grid, so the panoramic ribbon is tilted virtually in non-distorting manner. Alternatively, the unfolding of the arch in a straight line for generating the ribbon does not require applying a transformation grid. In other embodiments, the unfolding of the arch into the ribbon does not subsequently tilt to maximize frontal teeth apex perceptibility.

Figure 9:
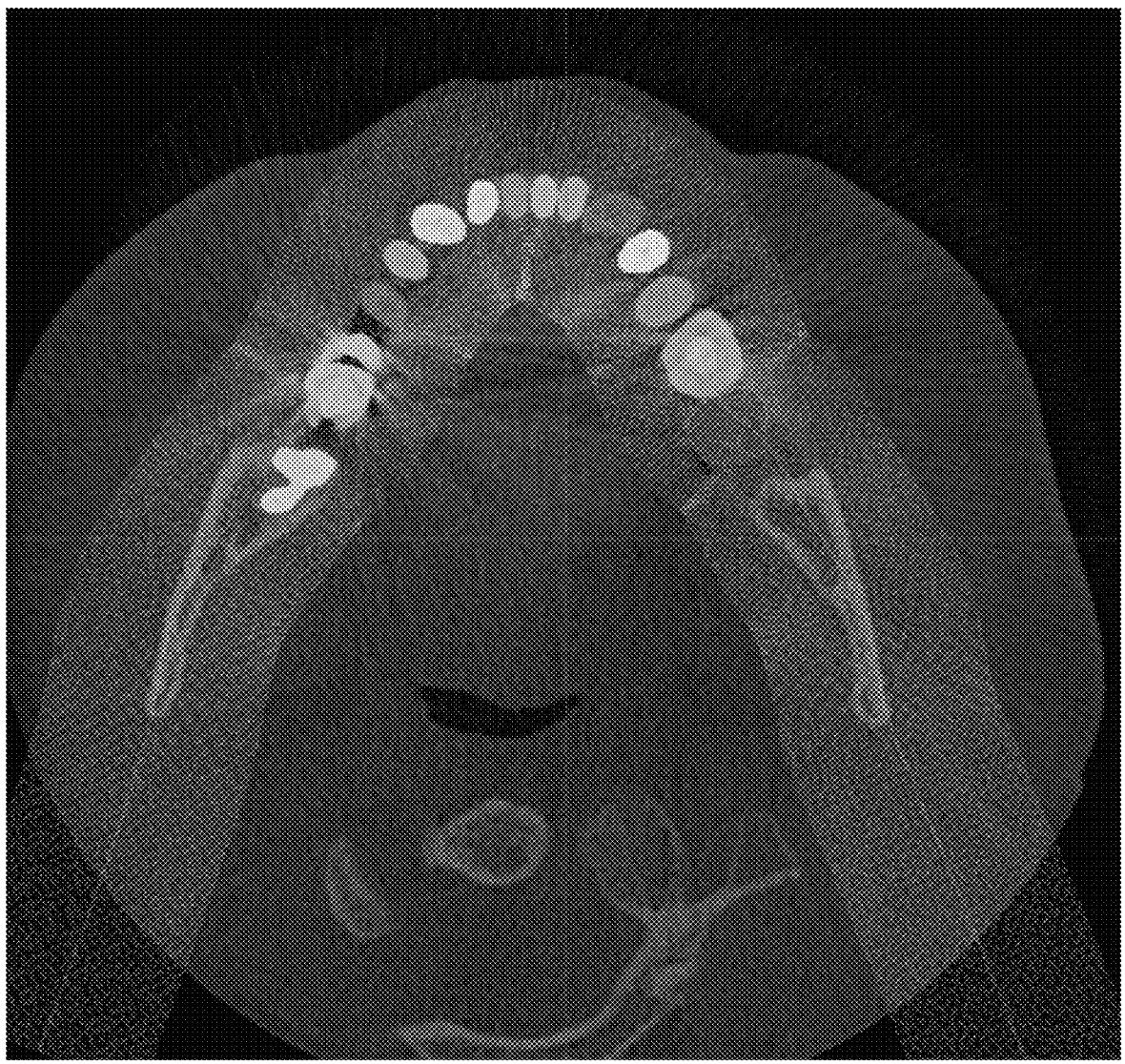
FIG. 9 illustrates in a screen-shot, an exemplary constructed panorama in accordance with an aspect of the invention.

During the second step we assign priorities to each point in panoramic ribbon. Priorities are defined as high in points that are inside or close to regions of interest (such as teeth, bone, and mandibular canals) and as low in points far from them. Final panoramic image is obtained by weighted summation in the direction perpendicular to teeth arch, where weights are priorities. This results in a panorama where elements of interest are emphasized in non-distorting manner, as illustrated in FIG. 9 (screen-shot of an exemplary constructed EoI-focused panorama in accordance with an aspect of the invention). In general, two types of panoramas may be constructed using the above mentioned method: (1) a general panorama; and (2) a split panorama. A general panorama includes RoI for all the teeth present, a whole mandible with TMJs, and a lower part of maxilla with sinuses cropped to the middle. A split panorama is constructed for both jaws separately and is focused only on teeth—as shown in FIG. 9. Alternatively, a method for generating a split or general panorama may be done with the following steps, beginning with (1) combining teeth and mandible segmentations; (2) building an axial projection of segmentation combination; (3) building a skeleton of the axial projection; (4) dividing the skeleton into all possible paths; (5) taking a longest path; (6) ensuring that this path is long enough to cover TMJs, if they are present; (7) smoothing the path; and then (8) returning it as the teeth arch.

While not illustrated in FIG. 8, one embodiment of the method flow may entail: As a first step, receiving an i/v.i (image/volumetric image) further parsed into at least a single image frame field of view by the volumetric image processor. Optionally, the at least single image frame field of view may be pre-processed by controlling image intensity value by the volumetric image processor. As a next step, an anatomical structure residing in the at least single field of view is localized by assigning each p/v (pixel/voxel) a distinct anatomical structure ID by the voxel parsing engine. Next, all p/v belonging to the localized anatomical structure is selected by finding a minimal bounding rectangle around the p/v and the surrounding region for cropping as a defined anatomical structure by the localization layer. Optionally, a visual report may be reconstructed with defined and localized anatomical structure. Also optionally, conditions for each defined anatomical structure may be classified within the cropped image by the classification layer. Next, extracting a teeth arch from the localized image generated and unfolding the extracted teeth arch into a panoramic ribbon; and finally, assigning weighted priorities to at least two points in the panoramic ribbon, wherein priorities are weighted higher for points inside or proximal to elements of interest (EoI) and applying a weighted summation in a direction perpendicular to teeth arch resulting in the panorama with EoI emphasized.

Figure 10:
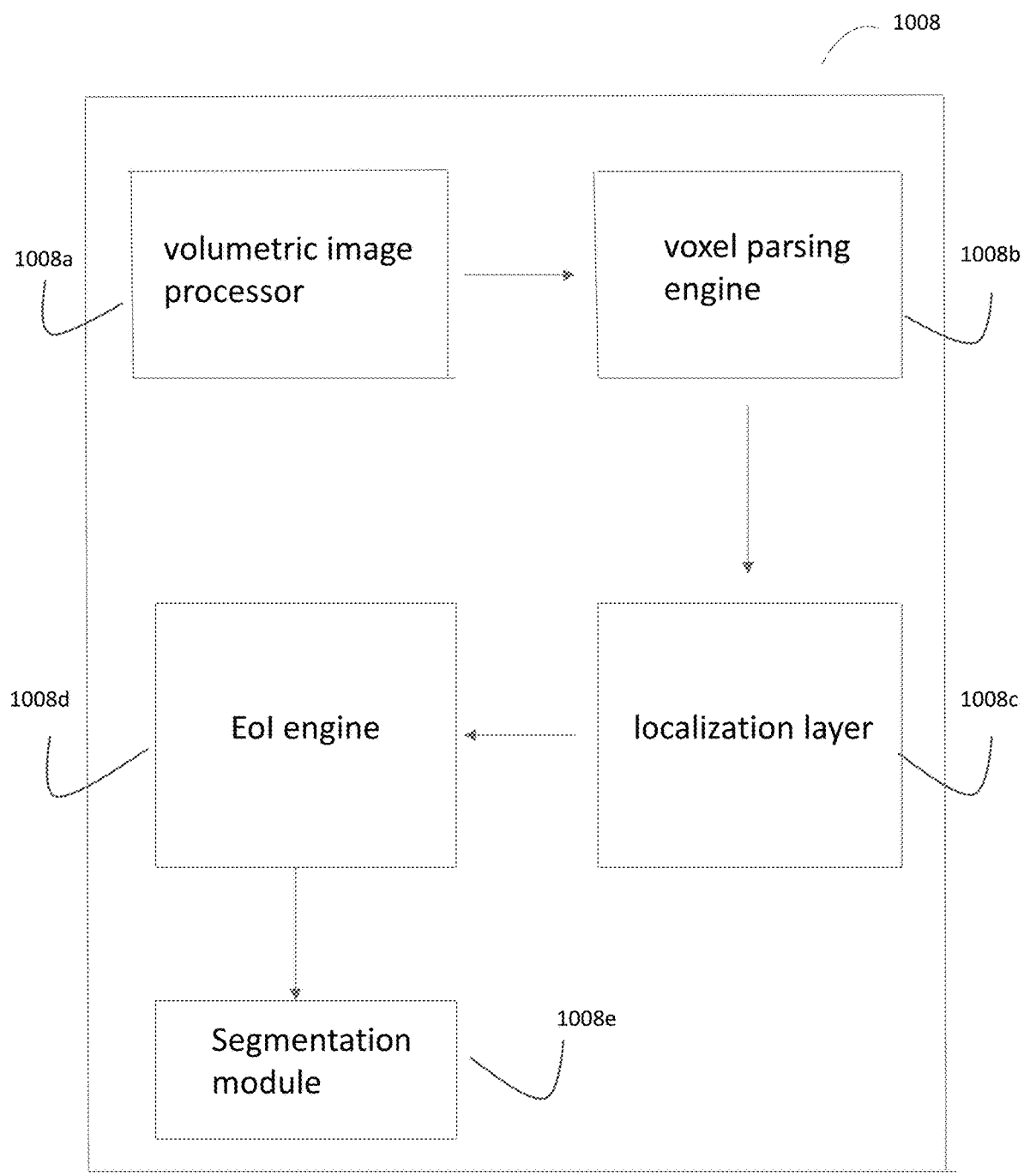
FIG. 10 depicts a system block diagram of the EoI-focused panorama construction in accordance with an aspect of the invention.

Now in reference to FIG. 10—depicting a system block diagram of the EoI-focused panorama construction in accordance with an aspect of the invention. A system for constructing an Elements of Interest (EoI)-focused panorama may comprise: a processor 1008; a non-transitory storage element coupled to the processor 1008; encoded instructions stored in the non-transitory storage element, wherein the encoded instructions when implemented by the processor 1008, configure the system to: extract a teeth arch from a volumetric image; unfold the extraction into a panoramic ribbon; assign weighted priorities to each point in the ribbon, wherein priorities are weighted higher for points inside or proximal to an EoI; and apply a weighted summation in a direction perpendicular to teeth arch, resulting in the panorama with the EoI emphasized.

As shown in FIG. 10, the system may comprise: a volumetric image processor 1008a, a voxel parsing engine 1008b, a localization layer 1008c, an EoI engine 1008d, an instance segmentation module 1008e, wherein the system, and more particularly, the EoI engine 1008d may be configured to: extract a teeth arch from a volumetric image; form a study image from the extract; unfold the study image into a panoramic ribbon; tilt the ribbon for maximal frontal teeth exposure; assign weighted priorities to at least two points in the ribbon, wherein priorities are weighted higher for points inside or proximal to EoI; apply a weighted summation in a direction perpendicular to teeth arch resulting in the panorama with EoI emphasized; and apply the instance segmentation module 1008e to accurately provide a segmentation mask and numbering with EoI emphasized.

In one embodiment, the teeth arch is extracted using segmentations of at least one of a teeth or anatomy by the EoI engine 1008d. Alternatively, the teeth arch extraction is done by an algorithm that combines teeth and mandible segmentations, extracts the teeth arch landmarks in 2D plane, fits a pre-defined function in form of a default teeth arch to the extracted landmarks, and returns a fitted function as the teeth arch. In one embodiment, the panoramic ribbon is a curved sub-volume passing along the teeth arch, created from unfolding the image of the extracted teeth arch. Alternatively, the extension of the teeth arch from 2D plane to 3D is done by an algorithm that extracts vestibuloral slices from a curved sub-volume of teeth and anatomy segmentations passing along the 2D teeth arch; construct a vertical curve that approximates position and tilt of upper and lower teeth and anatomy on each axial level at each vestibulooral slice; combine the extracted vertical curves in a way that points of each curve on each axial level resulting in a 2D teeth arch specific for a given axial level; and return a vertical curve combination as a 3D teeth arch.

In an embodiment, once the 3D panoramic ribbon is generated, priorities are assigned to a plurality of points arbitrarily chosen on the panoramic ribbon. The arbitrarily chosen points are evenly spaced along the length of the panoramic ribbon. In other embodiments, the points may not be chosen arbitrarily, but rather, according to a pre-defined rule. The elements of interest may be at least one of a bone, tooth, teeth, or mandibular canals. wherein weights are assigned highest to points inside or most proximal to elements of interest with a pre-defined highest value.

While not shown in FIG. 10, in another embodiment, the system may be configured to receive input image data from a plurality of capturing devices, or input event sources. A processor, including or in addition to, an image processor, a voxel parsing engine, a localization layer, and an EoI Engine may be comprised within the system. An image processor may be configured to parse the captured image into each image frame and, optionally, preprocess the parsed image. A voxel parsing engine may be configured to localize an anatomical structure residing in the at least single field of view by assigning each p/v a distinct anatomical structure ID. The localization layer may be configured to select all p/v belonging to the localized anatomical structure by finding a minimal bounding rectangle around the p/v and the surrounding region for cropping as a defined anatomical structure. Optionally, a detection module may be configured to detect the condition of the defined anatomical structure. Also, optionally, the detected condition could be sent to the cloud/remote server, for automation, to EMR and to proxy health provisioning. In another embodiment, detected condition could be sent to controllers, for generating reports and updates, dashboard alerts, export option or store option to save, search, print or email and sign-in/verification unit. Once localized, the EoI engine may be configured to: extract a teeth arch from the localized image; optionally, form a study image from the extract; unfold the extracted teeth arch, or optionally, the study image into a panoramic ribbon; tilt the ribbon for maximal frontal teeth exposure; assign weighted priorities to at least two points in the ribbon, wherein priorities are weighted higher for points inside or proximal to EoI; apply a weighted summation in a direction perpendicular to teeth arch resulting in the panorama with EoI emphasized; and, optionally, apply the instance segmentation module to accurately provide a segmentation mask and numbering with EoI emphasized.

In one embodiment, a segmentation module 1008e (optionally, an instance segmentation module), operating over 2D panoramic image plane, provides accurate teeth segmentation masks and numbering to a corresponding 3D CBCT image. The initial step is to segment teeth instances on an automatically generated panoramic image. Using state-of-the-art 2D instance segmentation deep learning models (R-CNN detectors), 1) localize teeth in 2D bounding boxes; 2) assign a number to each detected tooth in accordance with the dental formula; and 3) provide accurate 2D masks to each detected tooth. To train 2D instance segmentation module, utilize the mixture of the annotated OPT and panoramic images generated from CBCT, obtained as an output of our automatic panoramic generator. With the assistance of the 3D panoramic ribbon, retrieve 3D bounding boxes, inferred from the 2D panoramic instances, defining correspondence between 2D and 3D bounding boxes coordinates. The 3D bounding boxes (as regions of interest) are further submitted to 3D segmentation module, to obtain accurate 3D teeth masks in the original CBCT fine scale.

In further clarification, using one of the module's output (3D-UNet or 3D-R-CNN), use teeth masks to automatically construct panoramic surface, which defines mathematically; independently project the 3D tooth masks of both modules on a panoramic surface which gives 2D tooth masks projections. In order do this, calculate normal vectors to the panoramic surface and project every pixel of a mask on this surface. In parallel with the previous step, apply the third, 2D R-CNN style instance segmentation model, to the generated panorama image to acquire 2D tooth masks and labels. For every 2D R-CNN mask, pick an instance either from 3D-UNet or 3D-R-CNN. This step is accomplished by calculating an Intersection over Union (IoU) for 2D masks and the projected 3D masks, selecting the best 3D projections for every 2D instance on the panoramic image detected by 2D R-CNN detector. Since the relations between the 3D projected masks and the 3D masks themselves are understood, picking a 3D projected mask infers picking the corresponding 3D mask.

In one embodiment, the segmentation module 1008e (optionally, semantic segmentation modules or 3D U-Nets) is configured to specifically segment localized pathologies, like caries and periapical lesions. We use these segmentation to 1) estimate volume of the lesions to track it size dynamic over time, 2) create very specific visualizations (slice that cuts right at the maximum volume of the lesion), 3) get a "second opinion" network for diagnostics. These networks could also be trained in multi-task fashion, where one network learns to segment multiple types of lesions. A classification module could also be attached to the outputs of any network layer(s) to produce probabilities for lesion or whole-image. In case of whole-image classifier, it could be used to add cheaper weakly labeled data (single whole-image label "image contains lesions"/"image does not contain lesions") to costly segmentation labels (assigning lesion/background to each voxel). These networks typically operate on RoI defined by tooth sub-volume, like the Descriptor. However, non-dental diseases such as tumors and cysts in the jaws may also be diagnosed. In those cases, different RoI, like RoI of the upper/lower jaw, may be used.

Besides teeth, an anatomy of the skull may be segmented: Mandible and maxilla mandibular canal Sinuses, for instance. The combination of anatomy, along with teeth, may be exported as STL models to third party applications. The segmentation of mandibular canal to characterize a tooth's relation with it, e.g. "tooth is really close to canal", may be performed. This is relevant for surgery planning and diagnostics. Furthermore, a mandible and maxilla segmentation may be performed to diagnose gum disease and to select RoI for additional processing (e.g. tooth segmentation). Even furthermore, sinuses may be segmented to select RoI for sinus diagnosis.

A root-canal system localization module may be used to accurately segment all roots, canals inside them and pulp chamber for each presented tooth. A 3D U-Net based CNN architecture may be used to solve a multiclass semantic segmentation problem. Precise roots and canals segmentation affords a diagnostician/practitioner to estimate canals length, their curvature and visualize the most informative tooth slices in any point, direction, and with any size and thickness. This module allows to see and understand the anatomy of dental roots and canals and forms the basis for planning an endodontic treatment.

Gum disease is a loss of bone around a tooth. Inflammation around teeth may cause bone to recede and expose a tooth's roots. Gum disease diagnosis is performed by measuring a bone loss from a cemento-enamel juntion (CEJ, line on tooth's crown where enamel ends) to the beginning of bone envelope. Diagnosis is performed by segmenting 1) tooth's body, 2) enamel, 3) alveolar bone (tooth's bony envelope), and then algorithmically measuring what part of a tooth between apex and CEJ is covered by the bone.

These are two types of artefacts that may corrupt an image, rendering it unusable for diagnostic purposes. A model developed takes in 2D axial patches, centered on teeth, and predicts if the given CBCT is affected by an artefact, and also predicts the intensity of an artefact. If this probability is high, re-taking the image is recommended. In extreme cases, an intensity score may be assigned corresponding to the severity of the artefact.

A model developed finds locations of cephalometric landmarks on CBCT. Based on this, a calculation of cephalometric measurements may be preformed, which are relations (distances and angles) between sets of landmarks. Based on measurements, a screening may be performed, which may signal if patient might have an aesthetic/functional orthodontic problem and would benefit from a consult with an orthodontic.

A report that serves as a guide for implantology planning for a specific area has also been developed. A report consists of a panorama and a group of vestibular slices. A panorama may be constructed using virtual rotation that aligns occlusal plane. A panorama serves as a topogram that shows the locations of every slice. Slices have a tilt that is intended to match the implant placement direction. Some of the slices are provided with measurements that are present only if there is a place for implant. The distance can be estimated 1) as a horizontal plate situated in the implant entrance area that is usually tilted in the implant placement direction, 2) from the center of the plate to the closest point of either mandibular canal or maxillary sinus, 3) as a vertical from the oral end of plate to the farthest point of mandible.

Also developed is an endodontic treatment planning report generated from an uploaded CBCT image and chosen area of interest on the dental formula. A series of slices are then obtained: axial, cross-sectional canal shape, periapical lesions, C-shaped root canal, and root furcation. The report consists of several modules: the panoramic image of upper and/or lower jaw (depends on the region of interest), root canal space, root canal system, root canal shape, function, and periapical lesions. Optionally, a root canal system anatomy may be assessed and an evaluation of possible endodontic pathology. Further optionally, a report may be generated, which can be stored or handed over to the patient.

A report may be generated that provides necessary visual information about a specific third molar using the knowledge of tooth location. A report consists of three slice sections that differ in slice orientation: vestibular, axial, and mesiodistal slices. Every slice section has a topogram image that shows slice locations. A mandibular canal segmentation may be performed to visualize its location on topograms to notify a surgeon about tooth-canal relation.

As a part of mandible/maxilla, TMJ parts: Condyle and temporal bone (this step is optional, landmarks could be detected) may be segmented. Then, several landmarks on condyle and temporal bone may be detected and distances between them measured. These measurements and their relations, e.g. asymmetry, may be a basis for TMJ diagnosis and referral for additional study via MRI. TMJ disorders can cause pain and are typically counter-indications for orthodontic treatment.

Similar to pathology localizers, a model has been developed that will segment pathologies on panoramic radiograph. It operates over the entire image or inside a tooth RoI (bounding box predicted by OPT localizer). Any type of 2D segmentation network can be used, e.g. UNet. After pathology segmentation is obtained, assign pathologies to tooth by selecting those that are inside predicted tooth mask or are immediately adjacent to it.

Superimposition of several CBCTs are important for assessing changes between two time points. This may be performed in one of the following ways:
1) General SI: predict ceph landmarks and orient one image onto another by minimizing the distance between individual ceph points on the image.
2) During superimposition, some landmarks can be ignored if they are significantly changed, i.e., we minimize distance between points EXCEPT N points that have maximum distances after algorithm has converged.
3) Tooth-related SI: predict some tooth landmarks, like apex/radix points, furcation points, crown "bumps" and "fissures". Then do minimization of distances.
4) Generic mask-based SI: select some region, e.g., region around the tooth, and segment anatomy in it. Put a fine grid over this region. For each grid point, see which anatomical area is detected there. Then do SI by minimizing distances between all similar anatomical regions and maximizing distance between dissimilar ones.

A localizer-descriptor pipeline for segmentation of teeth+ detection of pathologies for intraoral x-rays (bitewing, periapical, occlusal images) has also been developed. The pipeline is similar to the CBCT/OPT described above (localizer/ descriptor pipeline). The pipeline may also be configured for segmentation of teeth+detection of pathologies for intraoral photography (optical-visible light-based). Developed also is a localizer-descriptor pipeline for segmentation of teeth+ detection of pathologies for intraoral optical scans (3D surface obtained with highly precise laser depth sensor and configured for optical texture-visible light-display).

Developed is a module that creates 3D models from tooth and anatomy masks. It uses marching cubes algorithm followed by laplacian smoothing to output a 3D mesh, which is later saved to STL. Certain anatomical objects can be grouped together to provide a surface containing selected objects (e.g. jaw+all teeth except one that is marked for extraction, for the purposes of a separate 3D-printing a surgical template for precise drilling of the implant hole).

Finally, a module that co-registers CBCT and IOS taken at the same time has been developed: Input is CBCT and IOS in separate coordinate systems. The output is IOS translated to coordinate system of CBCT. IOS have higher resolution, while CBCT displays the insides of the tooth/jaw. This is achieved by detecting the same dental landmarks (distinct points on teeth) on CBCT and IOS; at which point, minimize the distance between same points on CBCT and on IOS, which will give a coordinate transform to apply to IOS.

Advantageously, the present invention provides an end-to-end pipeline for detecting state or condition of the teeth in dental 3D CBCT scans. The condition of the teeth is detected by localizing each present tooth inside an image volume and predicting condition of the tooth from the volumetric image of a tooth and its surroundings. Further, the performance of the localization model allows to build a high-quality 2D panoramic reconstruction—with EoI focused—which provides a familiar and convenient way for a dentist to inspect a 3D CBCT image. The performance of the pipeline—with image processor, parsing engine, localization layer, EoI engine, and segmentation modules—is improved by adding i/v.i data augmentations during training; reformulating the localization task as instance segmentation instead of semantic segmentation; reformulating the localization task as object detection, and use of different class imbalance handling approaches for the classification model. Alternatively, the jaw region of interest is localized and extracted as a first step in the pipeline. The jaw region typically takes around 30% of the image/image volume and has adequate visual distinction. Extracting it with a shallow/ small model would allow for larger downstream models. Further, the diagnostic coverage of the present invention extends from basic tooth conditions to other diagnostically relevant conditions and pathologies.

Figure 11:
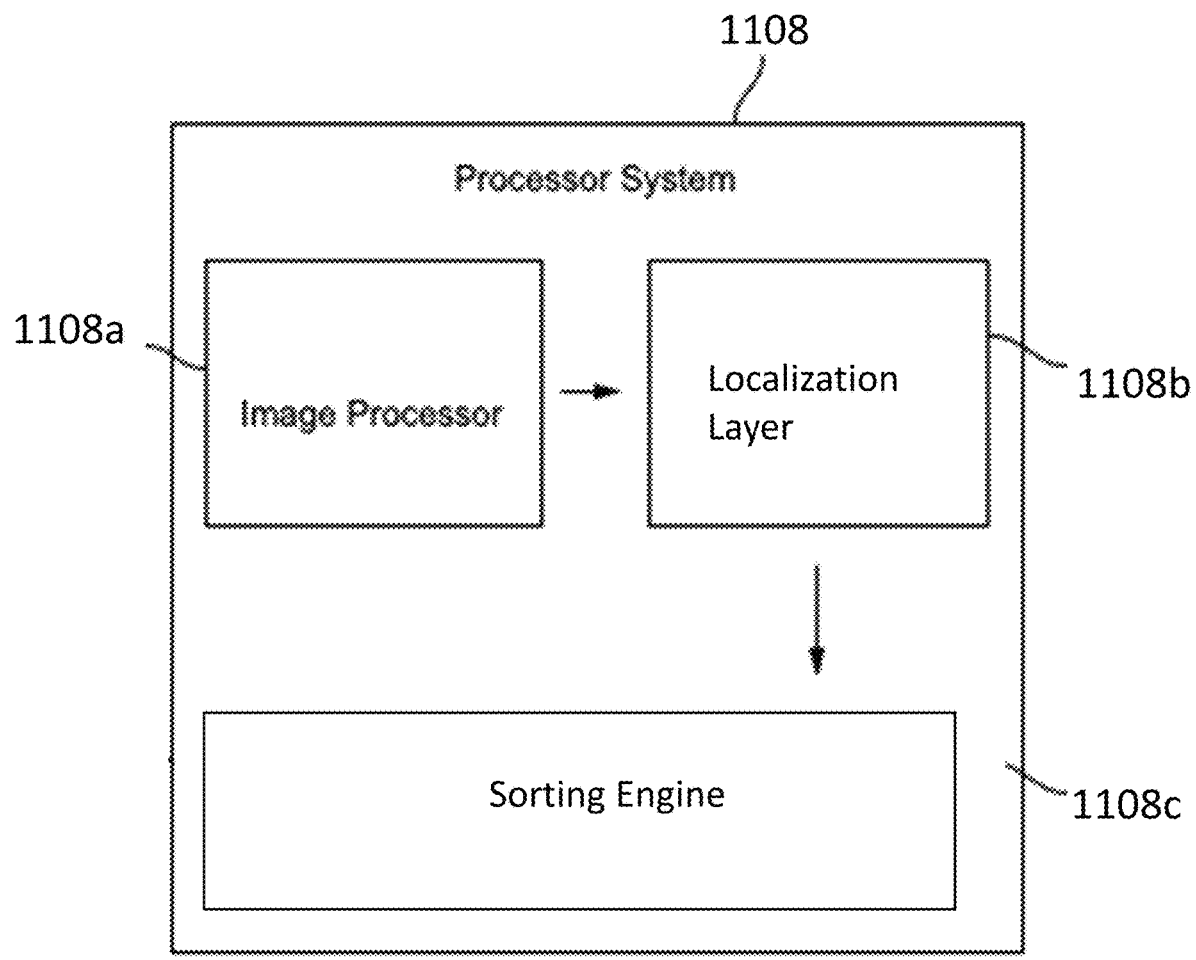
FIG. 11 illustrates in a block diagram, an automated system for localizing and enumerating dental images according to an embodiment.

FIG. 11 illustrates in a block diagram, a localizer-descriptor pipeline for segmentation of teeth and (optionally) detection of pathologies for intraoral x-rays (bitewing, periapical, occlusal images) and/or panoramics. The localizer-descriptor pipeline, illustrated in system block form in FIG. 11, may also be referred to as an automated tooth localization and enumeration system in accordance with an aspect of the invention. The pipeline/system is similar to the CBCT/OPT described above (localizer/descriptor pipeline). The system may also be configured for segmentation of teeth+detection of pathologies for intraoral photography (optical-visible light-based). The segmentation of teeth+detection of pathologies for intraoral optical scans (3D surface obtained with highly precise laser depth sensor and configured for optical texture-visible light-display) may also be implemented by the pipeline/system as described herein and as illustrated in FIG. 11.

In an exemplary embodiment—as shown in FIG. 11—the system may comprise an input system, an output system, a memory system or unit, a processor system 1108, an input/ output system and an interface. The processor system 1108 may comprise an image processor 1108a, (optionally) a parsing engine in communication with the image processor 1108a, a localization layer 1108b in communication with the parsing engine (optional) and/or image processor 1108a. The processor 1108 is configured to receive at least one 2-D image (radiographic or digital) via an input system. At least one received radiographic or digital 2-D image (2-D R/D) may, optionally, have its pixel array pre-processed to convert into an array of Hounsfield Unit (HU) radio intensity measurements. Then, the processor 1108 may optionally be configured to parse the received 2-D R/D into at least a single image frame field of view by the said image processor 1108a.

The anatomical structures residing in the at least single field of view or whole image is localized by assigning each pixel a distinct anatomical structure by the localization layer 1108b, or optionally, by the parsing engine. The processor 1108 or localization layer 1108b is configured to select all pixels belonging to the localized anatomical structure by finding a minimal bounding rectangle around the pixels and the surrounding region for cropping as a defined anatomical structure by the localization layer 1108b. In some embodiments. The pipeline/system may additionally segment pathologies on a 2-D R/D over an entire image and/or a cropped image of defined anatomical structure as defined by the localizer using a detection module/layer, such as a 2-D instance segmentation module (2-D R-CNN) (not shown).

FIG. 11 illustrates an exemplary automated tooth localization and enumeration system. The system may comprise: an image processor 1108a; a localization layer 1108b; a sorting engine 1108c; a processor 1108; a non-transitory storage element coupled to the processor; encoded instructions stored in the non-transitory storage element, wherein the encoded instructions when implemented by the processor 1108, configure the system to: receive a series of at least one of an intra-oral or panoramic images constituting a full mouth series (FMX) from a radio-image gathering or digital capturing source for processing by the image processor 1108a; parse the series of images into at least a single image frame field of view by said image processor 1108a; localize and enumerate (annotate) at least one tooth residing in the at least single image frame field of view by assigning each pixel a distinct tooth structure by selecting all pixels belonging to the localized tooth structure by finding a minimal bounding rectangle around the pixels and the surrounding region for cropping as a defined enumerated tooth structure image by the localization layer 1108b; and sort images using the defined enumerated tooth structure images to fill an FMX ((full mouth series) mounting table by the sorting engine 1108c.

In one embodiment, the localization layer 1108b includes 33 class semantic segmentation in 2-D. In one embodiment, the system is configured to classify each pixel as one of 32 teeth or background and resulting segmentation assigns each pixel to one of 33 classes. In another embodiment, the system is configured to classify each pixel as either tooth or other anatomical structure of interest. In case of localizing only teeth, the classification includes, but not limited to, 2 classes. Then individual instances of every class (teeth) could be split, e.g. by separately predicting a boundary between them. In some embodiments, the anatomical structure being localized, includes, but not limited to, teeth, upper and lower jaw bone, sinuses, lower jaw canal and joint.

In one embodiment, the system utilizes fully-convolutional network. In another embodiment, the system works on downscaled images and grayscale (1-channel) image (say, 1×100×100-dimensional tensor). In yet another embodiment, the system outputs 33-channel image (say, 33×100×100-dimensional tensor) that is interpreted as a probability distribution for non-tooth vs. each of 32 possible (for adult human) teeth, for every pixel.

In an alternative embodiment, the system provides 2-class segmentation, which includes labelling or classification, if the localization comprises tooth or not. The system additionally outputs assignment of each tooth pixel to a separate "tooth instance".

In one embodiment, the system comprises FCN/CNN (such as U-Net) predicting multiple "energy levels", which are later used to find boundaries. In another embodiment, a recurrent neural network could be used for step by step prediction of tooth, and keep track of the teeth that were outputted a step before. In yet another embodiment, Mask-R-CNN generalized to 2-D may be configured to take multiple crops from 2-D image in original resolution, perform instance segmentation, and then join crops to form mask for all original image. In another embodiment, the system could apply either segmentation or object detection in 2-D, to perform localization, enumeration or disagnostic functions. Furthermore, this would allow to process images in original resolution (albeit in 2D instead of 3D) and then infer 3D shape from a 2D segmentation.

In one embodiment, using any one of a pixel-level prediction technique, a tooth structure may be localized and enumerated within a cropped image from a full mouth series, wherein the condition is detected by at least one of detecting or segmenting a condition on at least one of the enumerated tooth structures within the cropped image. Localization may be improved by adding i/v.i data augmentations during training; reformulating the localization task as instance segmentation instead of semantic segmentation; reformulating the localization task as object detection, and use of different class imbalance handling approaches for the classification model. As a further method of improving localization, the jaw region of interest is localized and extracted as a first step in the pipeline. The jaw region typically takes around 30% of the image/image volume and has adequate visual distinction. Extracting it with a shallow/small model would allow for larger downstream models.

Figure 17:
FIG. 17 illustrates in a screenshot, an example of a localized and annotated tooth/teeth in an embodiment of the present invention.

While not shown, the system may further comprise a parsing engine or module, wherein parsing is achieved by taking input images (2-D R/D) and transform the images to a gray-scale pixel intensity matrices, suitable for subsequent processing by a convolutional neural network (CNN) for downstream localization, enumeration, or condition detection. Localization may be achieved by performing object detection and/or subsequent semantic segmentation of any tooth using any kind of object detection CNN—trained on a dataset of x-rays with teeth annotated using at least one of bounding boxes or pixel-wise masks. FIG. 17 illustrates an exemplary screen shot of a localized 2-D R/D image having been localized via the 2-D R-CNN-mediated object detection and/or semantic segmentation (localization layer). As FIG. 17 illustrates, the practitioner may click on any tooth/tooth number (localized/enumerated) for spotlight, validation, or further diagnostic prompting.

While not shown, the system may further comprise an enumeration layer, achieving enumeration by performing at least one of a direct classification approach, separate model classification branches, or a semantic segmentation sub-model. For example, in the first approach (direct classification), directly classify the number of tooth (1-52, 1-32 for permanent dentition, 33-52 for primary dentition). For the second approach (separate model classification), use separate model classification branches (heads, subunits) to identify: 1) anatomical tooth number (1-8); 2) whether the tooth is primary or permanent; 3) whether the tooth is live tooth or a tooth-like construct (implant, pontic, etc.); 4) whether the tooth is primary (child/milk tooth) or permanent; 5) classifying anatomical side (left/right); and 6) classifying jaw (maxilla/mandible). With respect to the third approach (semantic segmentation sub-model), follow the second approach, but replace step 4)-6) with semantic segmentation sub-model that predicts pixel assignment to dental chart quarters 1-8 (4 for permanent, 4 for primary) for all teeth.

Regardless of what approach is employed, one may perform enumeration or classification on the tooth crop (minimal bounding box of the tooth); or significantly extend the crop with a surrounding image as a context (to capture details that could help the model with identifying the tooth's dental quarter); or finally, perform classification on the whole image, while passing a binary mask of the tooth we mean to classify as an additional feature (input image channel).

Figure 18:
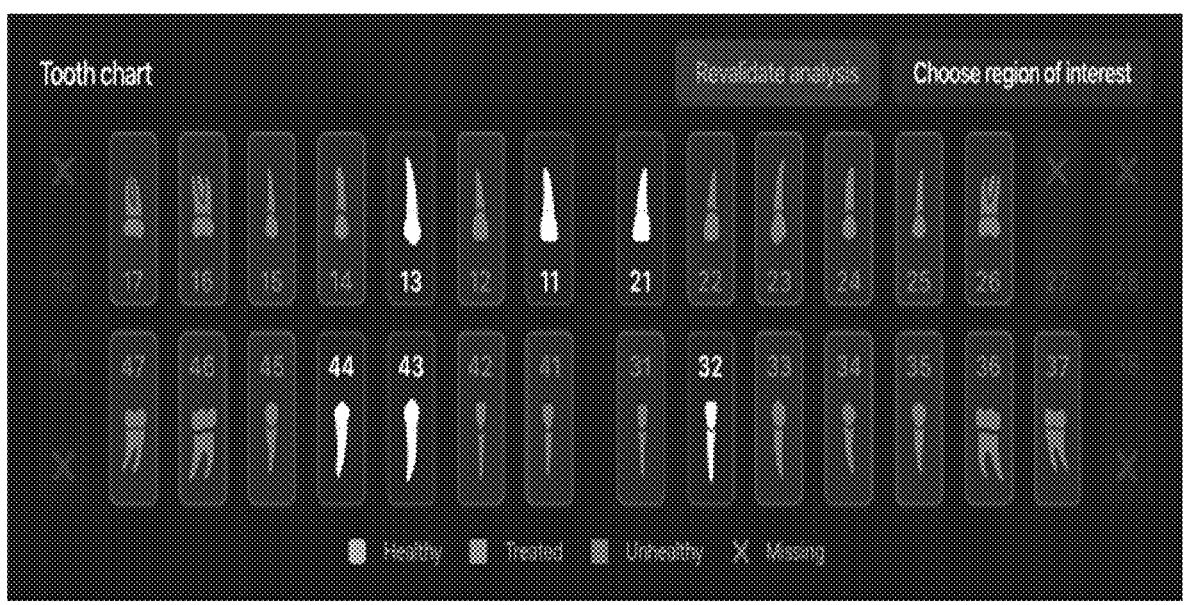
FIG. 18 illustrates in a screenshot, an example of a localized, annotated, and diagnosed tooth/teeth in an embodiment of the present invention.

The system may further comprise an enumeration post-processing layer, achieving enumeration post-processing by receiving input of predicted tooth numbers; re-orienting the image using a correct orientation prediction by a separate classification neural network; partitioning predicted tooth numbers in correct order; and reassigning numbers of incorrect numbers to get tooth order consistent with a standard tooth chart. FIG. 18 illustrates in a screenshot, an example of a localized and annotated (enumerated) tooth/teeth in an embodiment of the present invention. More crucially, it also annotates for unhealthy teeth. For instance, based on the data result of the localization and enumeration, tooth 23 appears to be annotated as unhealthy which may prompt further diagnostic evaluation.

Figure 16:
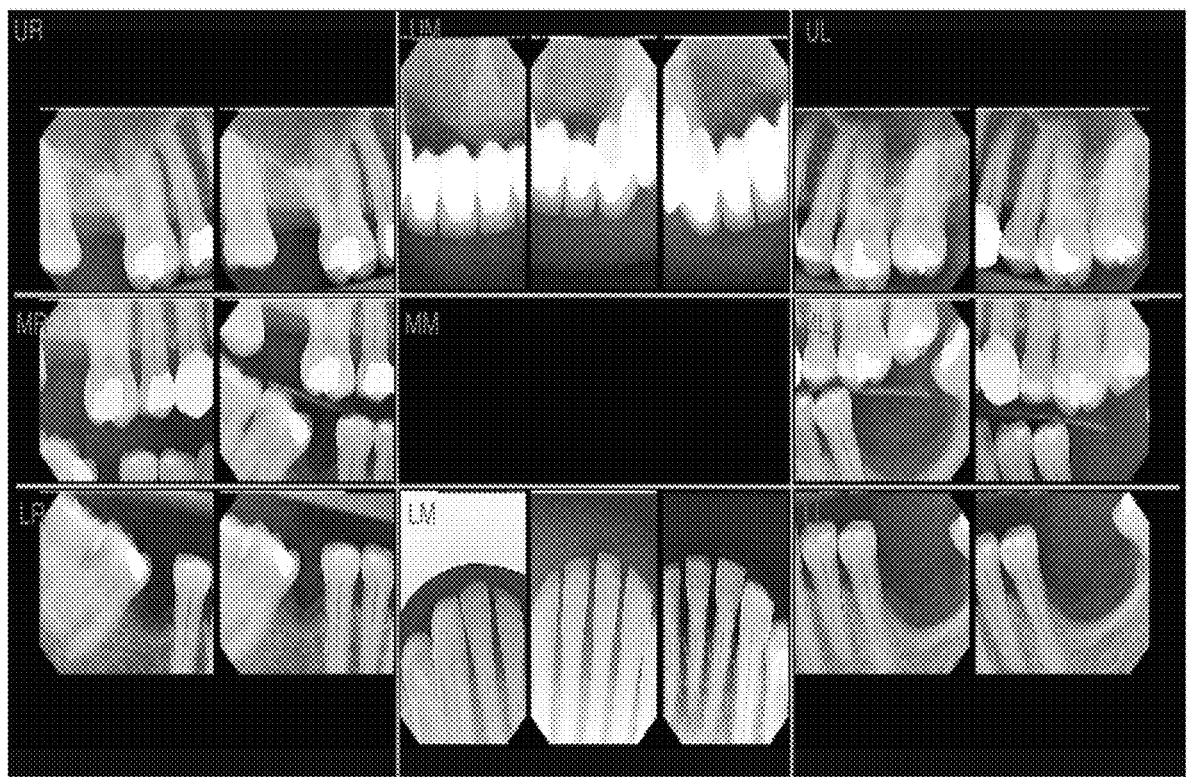
FIG. 16 illustrates in a screenshot, an example of a sorted image according to an embodiment of the present invention.

Furthermore, sorting may be achieved by the sorting engine 1108c as shown in FIG. 11. The sorting engine 1108c achieves sorting by first receiving average signed anatomical tooth number (from −8 to 8, ignoring the tooth quadrant) for each image; then partitioning images into nine location-based partitions: UR-UM-UL-MR-MM-ML-LR-LM-LL (as shown in FIG. 16—illustrating in a screenshot, an example of a sorted image) based on a set of anatomical tooth numbers identified on the image, where upper row receives images with only maxillary teeth, lower row (LR-LM-LL) receives images with only mandibular teeth, middle row receives images with a mix of maxillary and mandibular teeth; and patient-right (UR-MR-LR) side receives images that display only teeth from the right side of the patient face, patient-left (UL-ML-LL) side receives images that display only teeth from the left side of the patient face, and middle side (UM-MM-LM) receives images containing a mix of both left and right teeth; and then ordering and sorting images using that number in ascending order. While not shown, some embodiments additionally include a validation module, wherein validation is achieved by studying the preliminary matrix of numbered teeth, looking for teeth that are out of order, and if out of order, reassigning the tooth number and re-sorting the matrix. Validation may additionally be performed by the practitioner and requested to confirm prior to moving to next slide—as indicated in the lower left region of FIG. 17 and top right region of FIG. 18. In another embodiment, partitioning images between patient right, middle and left sides are achieved by establishing upper and lower bounds on average signed anatomical tooth number, such as values below −3 are assigned to patient-right side partitions; values between −3 and 3 are assigned to middle partitions; values above 3 are assigned to patient-left partitions, where three [3] is a constant that could be any number.

Furthermore, sorting is achieved by the sorting engine 1108c as shown in FIG. 11. The sorting engine 1108c achieves sorting by partitioning teeth into nine location-based partitions: UR-UM-UL-MR-MM-ML-LR-LM-LL; and then ordering within each partition by first receiving average signed anatomical tooth number for each side; and then sorting images using that number in ascending order. While not shown, some embodiments additionally include a validation module, wherein validation is achieved by studying the preliminary matrix of numbered teeth, looking for things that are out of order, and if out of order, reassigning the number and re-sorting the matrix. Validation may additionally be performed by the practitioner and requested to confirm prior to moving to next slide—as indicated in the lower left region of FIG. 17 and top right region of FIG. 18.

Figure 12:
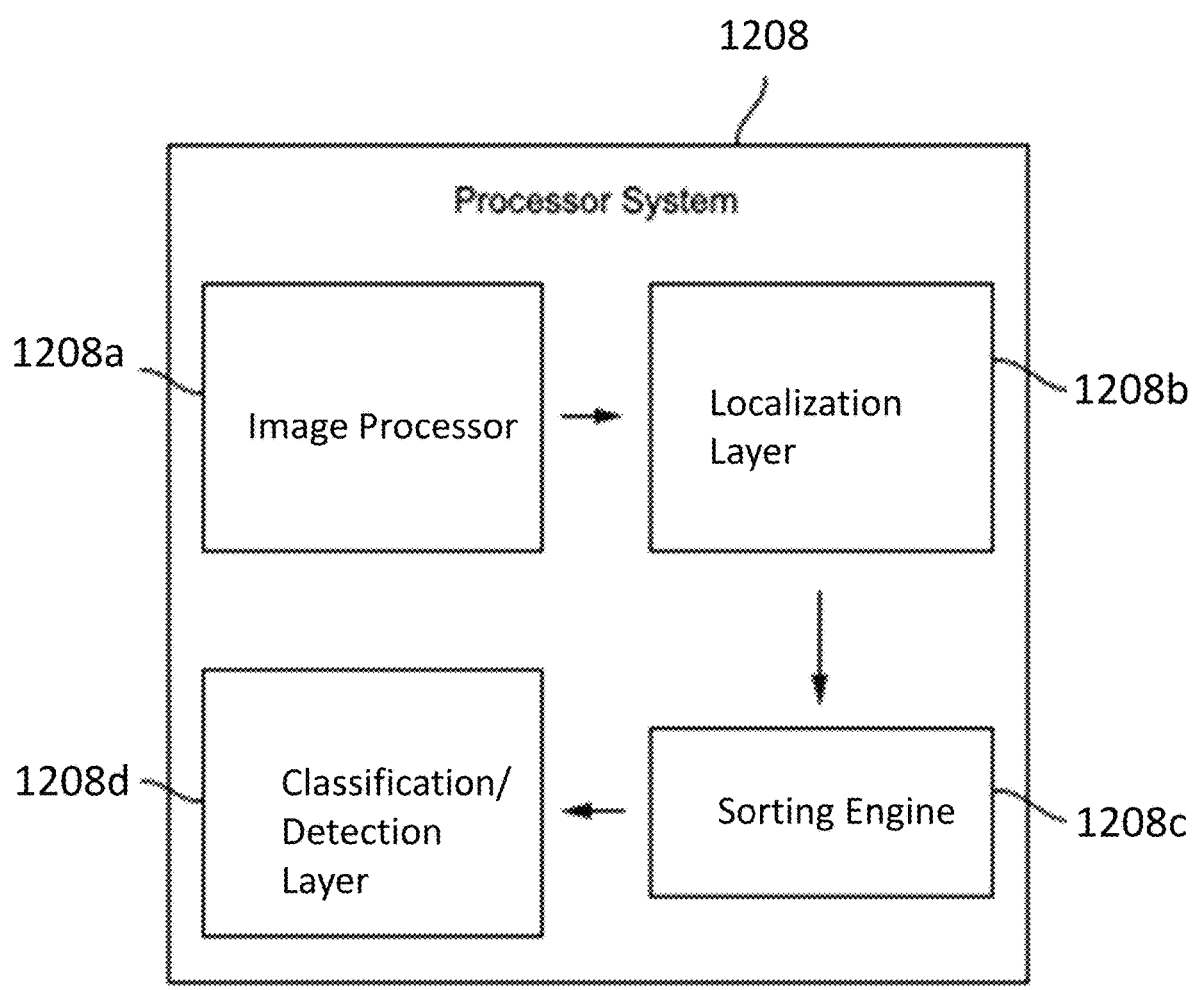
FIG. 12 illustrates in a block diagram, an automated system for localizing, enumerating, and diagnosing tooth conditions from dental images according to an embodiment.

FIG. 12 illustrates in a block diagram, an automated system for localizing, enumerating, and diagnosing tooth conditions from dental images according to an embodiment. In one embodiment, the system may comprise: an image processor 1208a configured for processing at least one of an intra-oral or panoramic x-ray image; optionally, a parsing module/image processor to parse the series of images into at least a single image frame field of view by the image; a localization layer 1208b; optionally, a sorting engine using the defined enumerated tooth structure image to fill an FMX (full mouth series) mounting table; a classification/detection layer 1208d; a processor 1200; a non-transitory storage element coupled to the processor 1200; encoded instructions stored in the non-transitory storage element, wherein the encoded instructions when implemented by the processor 1200, configure the system to: receive a series of images constituting a full mouth series from a radio-image gathering or digital capturing source by the image processor 1208a; localize and enumerate at least one tooth residing in at least single image frame field of view by assigning each pixel a distinct tooth structure by selecting all pixels belonging to the localized tooth structure by finding a minimal bounding rectangle around said pixels and the surrounding region for cropping as a defined enumerated tooth structure image by the localization layer 1208b; optionally, sort the images to fill the FMX mounting table; and detect conditions for each defined enumerated tooth structure within a cropped image, wherein conditions are detected by the classification layer/module or detection layer/module 1208d, wherein the detection module 1208d at least one of detects or segments conditions and pathologies on at least one of the enumerated tooth structures within the cropped image.

In some embodiments, conditions may be detected by training a CNN to either detect (using object detection architectures) or segment (using multiple binary semantic segmentation architectures) conditions and pathologies on FMX, panoramics and various other crops with respect to partial or whole tooth/teeth. CNNs may be trained on many data sets containing different types of conditions in multi-task fashion. Each example is trained on only for conditions that are defined for it. Conditions that are not defined will be masked out (their per-condition loss is multiplied by 0 before back-propagating).

Figure 19:
FIG. 19 illustrates in a screenshot, an example of a localized, annotated, and diagnosed tooth/teeth in an embodiment of the present invention.

Some conditions may be related to whole tooth and are not localized to any specific area on the tooth. To detect such conditions, a standard full-image classification CNN on a tooth crop (with possible context extension) may be used for training. Examples of such conditions are: impacted tooth, dystonic tooth, (+degree of impaction), implant, pontic, etc. Further, the diagnostic coverage of the present invention extends from basic tooth conditions to other diagnostically relevant conditions and pathologies. FIG. 19 illustrates in a screenshot, an example of a localized, annotated, and diagnosed tooth/teeth in an embodiment of the present invention. It spotlights the unhealthy marked tooth 23 from FIG. 18, wherein the percentages or likelihood of certain conditions being present for tooth 23 are predicted. For example, tooth 23 has a 40% predictive likelihood of caries and a 48% predictive likelihood of having voids in a root canal filing.

In one embodiment, the system could be implemented utilizing descriptor learning in the multitask learning framework i.e., a single network learning to output predictions for multiple dental conditions. This could be achieved by balancing loss between tasks to make sure every class of every task have approximately same impact on the learning. The loss is balanced by maintaining a running average gradient that network receives from every class*task and normalizing it. Alternatively, descriptor learning could be achieved by teaching network on batches consisting data about a single condition (task) and sample examples into these batches in such a way that all classes will have same number of examples in batch (which is generally not possible in multitask setup). Further, standard data augmentation could be applied to tooth images to perform scale, crop, rotation, vertical flips. Then, combining all augmentations and final image resize to target dimensions in a single affine transform and apply all at once. In some embodiments, the system could use coarse segmentation mask from localizer as an input instead of tooth image. In some embodiments, the descriptor could be trained to output fine segmentation mask from some of the intermediate layers. In some embodiments, the descriptor could be trained to predict tooth number.

As an alternative to multitask learning approach, "one network per condition" could be employed, i.e. models for different conditions are completely separate models that share no parameters. Another alternative is to have a small shared base network and use separate subnetworks connected to this base network, responsible for specific conditions/diagnoses.

Similar to pathology localizers, a model has been developed that will segment pathologies on panoramic radiograph. It operates over the entire image or inside a tooth RoI (bounding box predicted by OPT localizer). Any type of 2D segmentation network can be used, e.g. UNet. After pathology segmentation is obtained, assign pathologies to tooth by selecting those that are inside predicted tooth mask or are immediately adjacent to it.

Furthermore, in one embodiment, the detection module 1208*d* may be coupled to a segmentation module (optionally, semantic segmentation modules or 2-D U-Nets), configured to specifically segment localized pathologies, like caries and periapical lesions. We use these segmentation to 1) estimate volume of the lesions to track it size dynamic over time; 2) create very specific visualizations (FIG. 18); 3) get a "second opinion" network for diagnostics. These networks could also be trained in multi-task fashion, where one network learns to segment multiple types of lesions. A classification or detection module 1208*d* could also be attached to the outputs of any network layer(s) to produce probabilities for lesion or whole-image. In case of whole-image classifier, it could be used to add cheaper weakly labeled data (single whole-image label "image contains lesions"/"image does not contain lesions") to costly segmentation labels (assigning lesion/background to each voxel). These networks typically operate on RoI defined by tooth sub-volume, like the Descriptor. However, non-dental diseases such as tumors and cysts in the jaws may also be diagnosed. In those cases, different RoI, like RoI of the upper/lower jaw, may be used.

Figure 13:
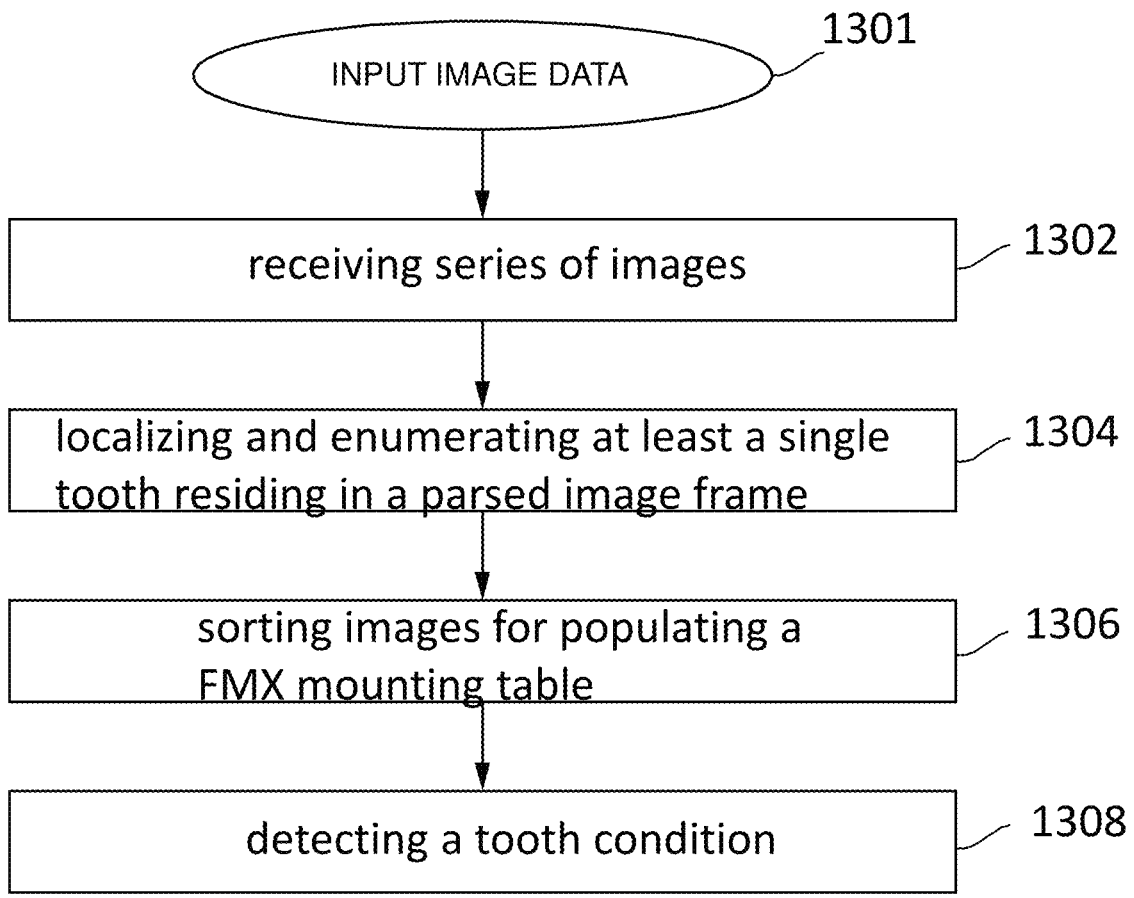
FIG. 13 illustrates in a method flow diagram, the steps for localizing, enumerating, and diagnosing tooth conditions from dental images according to an embodiment.
Figure 14:
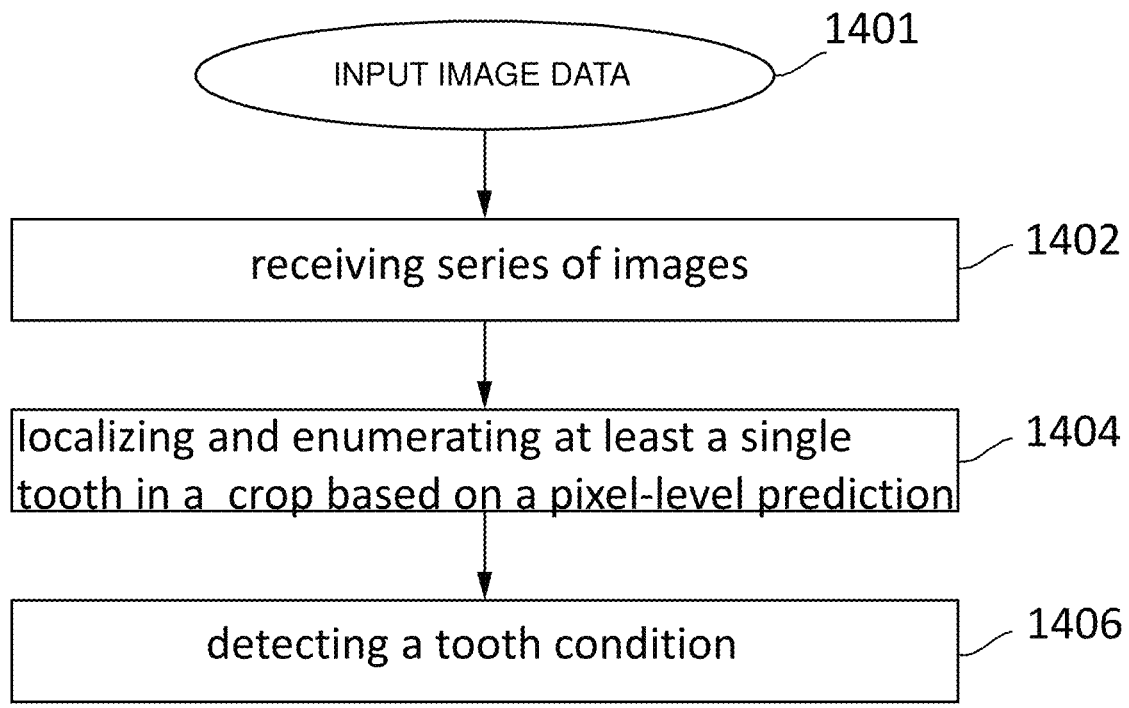
FIG. 14 illustrates in a method flow diagram, the steps for localizing, enumerating, and diagnosing tooth conditions from dental images according to an embodiment.

FIGS. 13 and 14 illustrate in method flow diagrams, an automated system for localizing, enumerating, and diagnosing tooth conditions from dental images according to an embodiment. FIG. 13 illustrates a method for tooth localization, enumeration, and diagnosing comprising the steps of: receiving a series of at least one of an intra-oral or panoramic images constituting a full mouth series from a radio-image gathering or digital capturing source for processing 1302; localizing and enumerating at least one tooth residing in at least single image frame field of view by assigning each pixel a distinct tooth structure by selecting all pixels belonging to the localized tooth structure by finding a minimal bounding rectangle around said pixels and the surrounding region for cropping as a defined enumerated tooth structure image 1304; sorting images using the defined enumerated tooth structure images to fill an FMX mounting table 1306; and detecting conditions for each defined enumerated tooth structure within a cropped image, wherein conditions are detected by at least one of detecting or segmenting conditions and pathologies on at least one of the enumerated tooth structures within the cropped image 1308.

FIG. 14 illustrates a method for automated localization, enumeration, and diagnosing of a tooth/condition. The method, as illustrated, comprises the steps of: receiving a series of at least one of an intra-oral or panoramic images constituting a full mouth series from a radio-image gathering or digital capturing source for processing 1402; localizing and enumerating at least one tooth structure residing in at least single cropped image based on a pixel-level prediction 1404; and detecting conditions for each defined enumerated tooth structure within the cropped image, wherein conditions are detected by at least one of detecting or segmenting conditions and pathologies on at least one of the enumerated tooth structures within the cropped image 1406.

In other embodiments, a method for automated localization and enumeration of a tooth is described. The method, while not illustrated, comprises the steps of: receiving a series of at least one of an intra-oral or panoramic images constituting a full mouth series from a radio-image gathering or digital capturing source for processing; and localizing and enumerating at least one tooth structure residing in at least single cropped image based on a pixel-level prediction.

The pixel-level prediction may be defined as any computer vision (C.V) task exploiting spatial redundancies in neighboring pixels resulting in image or object recognition/prediction based on an individual pixel within a broader pixel grouping (neighboring pixels). Examples of C.V. tasks include edge detection, object detection, convolutional networks, deep learning, semantic segmentation, etc.

Also, while not shown in FIG. 14, a method for automated localization, enumeration, and diagnosing of a tooth/condition may comprise the steps of: receiving a series of at least one of an intra-oral or panoramic images constituting a full mouth series from a radio-image gathering or digital capturing source for processing; and detecting conditions for each defined localized and enumerated tooth structure within a cropped image based on any one of a pixel-level prediction, wherein conditions are detected by at least one of detecting or segmenting conditions and pathologies on at least one of the enumerated tooth structures within the cropped image.

Figure 15:
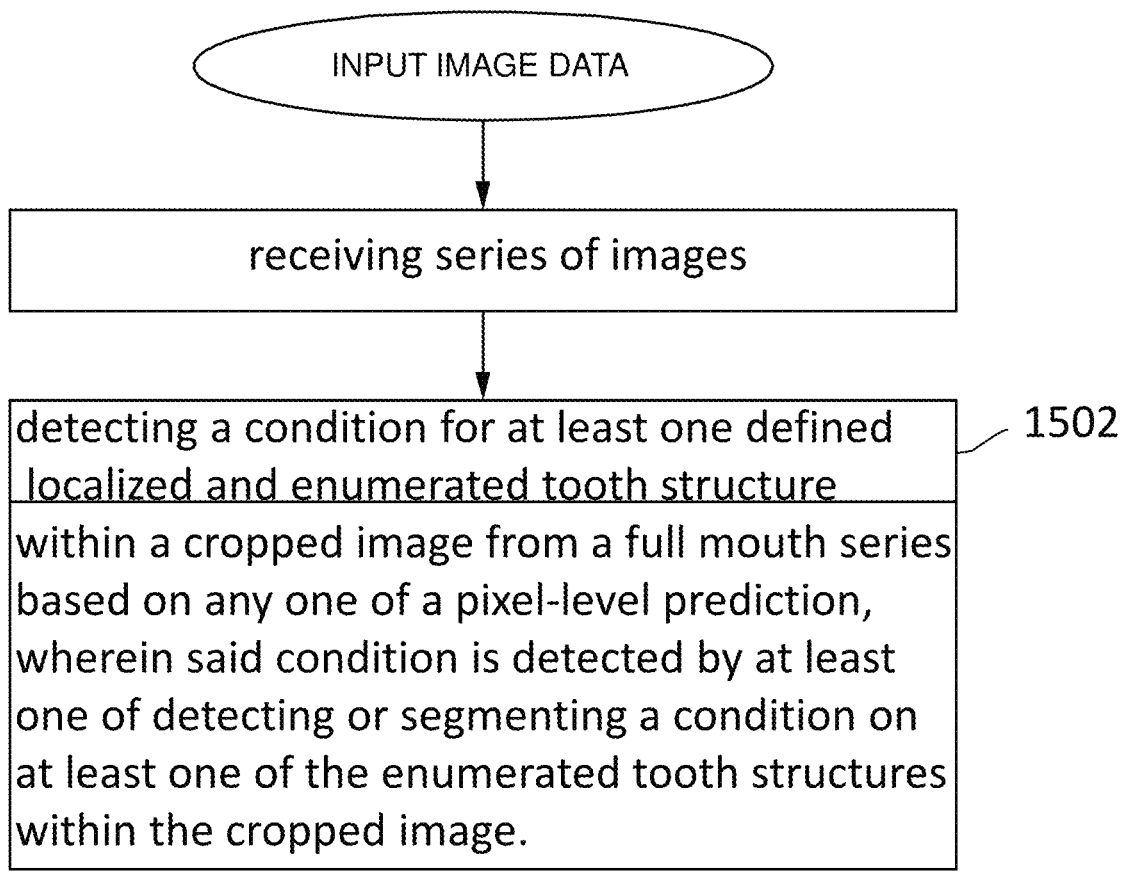
FIG. 15 illustrates in a method flow diagram, the steps for localizing, enumerating, and diagnosing tooth conditions from dental images according to an embodiment.

FIG. 15 illustrates a method for automated localization, enumeration, and diagnosing of a tooth/condition, said method comprising the step of: detecting a condition for at least one defined localized and enumerated tooth structure within a cropped image from a full mouth series based on any one of a pixel-level prediction, wherein said condition is detected by at least one of detecting or segmenting a condition on at least one of the enumerated tooth structures within the cropped image 1502.

The figures illustrate the architecture, functionality, and operation of possible implementations of systems, methods and computer program products according to various embodiments of the present invention. It should also be noted that, in some alternative implementations, the functions noted/illustrated may occur out of the order noted. For example, two blocks shown in succession may, in fact, be executed substantially concurrently, or the blocks may sometimes be executed in the reverse order, depending upon the functionality involved.

Since various possible embodiments might be made of the above invention, and since various changes might be made in the embodiments above set forth, it is to be understood that all matter herein described or shown in the accompanying drawings is to be interpreted as illustrative and not to be considered in a limiting sense. Thus, it will be understood by those skilled in the art that although the preferred and alternate embodiments have been shown and described in accordance with the Patent Statutes, the invention is not limited thereto or thereby.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Additionally, it is to be understood that references to anatomical structures may also assume image or image data corresponding to the structure. For instance, extracting a teeth arch translates to extracting the portion of the image wherein the teeth arch resides, and not the literal anatomical structure.

Some portions of embodiments disclosed are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media (e.g., read-only memory devices within a computer such as CD-ROM disks readable by a CD-ROM drive); (ii) alterable information stored on writable storage media (e.g., floppy disks within a diskette drive or hard-disk drive, solid state disk drive, etc.); and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, and composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

We claim:

1. A system for a localizer-descriptor pipeline for segmentation of teeth, said system comprising:
   an image processor;
   a localization layer;
   a sorting engine;
   a processor;
   a non-transitory storage element coupled to the processor;
   encoded instructions stored in the non-transitory storage element, wherein the encoded instructions when implemented by the processor, configure the system to:
   receive a series of at least one of an intra-oral or panoramic images from a radio-image gathering or digital capturing source for processing by the image processor;
   parse the series of images into at least a single image frame field of view by said image processor;
   localize and enumerate at least one tooth residing in the at least single image frame field of view by assigning each pixel a distinct tooth structure by selecting all pixels belonging to the localized tooth structure by finding a minimal bounding rectangle around said pixels and the surrounding region for cropping as a defined enumerated tooth structure image by the localization layer; and
   sort images using the defined enumerated tooth structure image to fill an FMX (full mouth series) mounting table by the sorting engine.

2. The system of claim 1, wherein parsing is achieved by taking input images and transforming said images to grayscale pixel intensity matrices, suitable for subsequent processing by a convolutional neural network (CNN).

3. The system of claim 1, wherein localization is achieved by performing object detection and subsequent semantic segmentation of any tooth using any kind of object detection CNN, wherein said CNN is trained on a dataset of x-rays with teeth annotated using at least one of bounding boxes or pixel-wise masks.

4. The system of claim 1, further comprising an enumeration layer, achieving enumeration by performing at least one of a direct classification approach, separate model classification branches, or a semantic segmentation sub-model.

5. The system of claim 1, further comprising an enumeration post-processing layer, achieving enumeration post-processing by receiving input of predicted tooth numbers; re-orienting the image using a correct orientation prediction by a separate classification neural network; partitioning predicted tooth numbers in correct order; and reassigning numbers of incorrect numbers to get tooth order consistent with a standard tooth chart.

6. The system of claim 1, wherein sorting is achieved by partitioning teeth in nine partitions:

Upper row-Upper Maxillary-Upper Left-Mandibular right-middle side-Mandibular left-Lower Row-Left Mandibular-Left Maxillary (UR-UM-UL-MR-MM-ML-LR-LM-LL);

and then ordering within each partition by first receiving average signed anatomical tooth number for each side; and then sorting images using that number in ascending order.

7. The system of claim 1, further comprising validation, wherein validation is achieved by studying the preliminary matrix of numbered teeth, looking for things that are out of order, and if out of order, reassigning the number and re-sorting the matrix.

8. The system of claim 1, further comprising a detection layer, wherein detection on a panoramic image is achieved by using a sliding window over a dentition region.

9. The system of claim 1, wherein the localization starts with a localization and extraction of a jaw region of interest prior to localizing the at least one tooth residing in the at least single image frame field of view.

10. The system of claim 1, further comprising a classification layer, wherein the classification layer detects conditions for each defined enumerated tooth structure within a cropped image.

11. The system of claim 10, wherein conditions are detected by training a CNN to at least one of detect or segment conditions and pathologies on at least one of the enumerated tooth structures within the cropped image.

12. The system of claim 10, wherein conditions that are not defined are masked out.

13. The system of claim 10, wherein the classification layer detects for a whole-tooth condition.

14. The system of claim 10, wherein the classification layer is coupled to any one of a network layer to perform at least one of the following diagnostics: probability of a pathology, volume of pathology, rate of progression or regression of pathology, creation of visual reports, and/or option to transmit at least one of the diagnostics to a second network for confirming said diagnostics.

15. The system of claim 1, further comprising pre-processing, wherein the pre-processing comprises using any one of a normalization schemes to account for variations in image value intensity depending on at least one of an input or output of the image.

* * * * *